(12) United States Patent
Ganesan et al.

(10) Patent No.: US 9,795,470 B2
(45) Date of Patent: Oct. 24, 2017

(54) AORTIC ARCH FILTRATION SYSTEM FOR CAROTID ARTERY PROTECTION

(71) Applicant: Lumen Biomedical, Inc., Maple Grove, MN (US)

(72) Inventors: Kavitha Ganesan, Maple Grove, MN (US); Matthew F. Ogle, Fitchburg, WI (US)

(73) Assignee: Lumen Biomedical, Inc., Fridley, MN (US)

( * ) Notice: Subject to any disclaimer, the term of this patent is extended or adjusted under 35 U.S.C. 154(b) by 93 days.

(21) Appl. No.: 13/742,760

(22) Filed: Jan. 16, 2013

(65) Prior Publication Data

US 2013/0184742 A1 Jul. 18, 2013

Related U.S. Application Data

(60) Provisional application No. 61/587,413, filed on Jan. 17, 2012, provisional application No. 61/661,643, filed on Jun. 19, 2012.

(51) Int. Cl.
*A61F 2/01* (2006.01)
*A61B 17/12* (2006.01)
(Continued)

(52) U.S. Cl.
CPC .......... *A61F 2/01* (2013.01); *A61B 17/12031* (2013.01); *A61B 17/12036* (2013.01);
(Continued)

(58) Field of Classification Search
CPC ..... A61M 25/04; A61M 25/1006; A61F 2/01; A61F 2/013; A61F 2002/011; A61F 2002/015; A61F 2002/016

See application file for complete search history.

(56) References Cited

U.S. PATENT DOCUMENTS 5,041,093 A * 8/1991 Chu .............................. 604/104
5,200,248 A 4/1993 Thompson et al.
(Continued)

FOREIGN PATENT DOCUMENTS

WO 2004/043293 A2 5/2004
WO 2006/023203 A1 3/2006
(Continued)

OTHER PUBLICATIONS

Fiber Innovation Technology: 4DG Fibers: http://web.archive.org/web/2011030070010/http://fitfibers.com/4DG_Fibers.htm; (Oct. 30, 2001).
(Continued)

*Primary Examiner* — Tuan V Nguyen
(74) *Attorney, Agent, or Firm* — Christensen, Fonder, Dardi & Herbert PLLC; Peter S. Dardi

(57) ABSTRACT

Filtration systems with integrated filter element(s) forming portions of the wall of the filtration catheter are disclosed. The filtration catheters disclosed herein are designed to be used alone or in conjunction with another filter device to provide embolic protection of both carotid arteries. Occlusive element such as balloon is placed on the exterior of the filtration catheter to redirect blood flow in the vessels during the filtration process as well as to help anchor the filtration catheter inside the vessel. The integrated filter element(s) does not require collapsing thus significantly reduces the complexity of the filtration system retrieval process and the chances of releasing emboli back into the blood stream. The compact design of the filtration systems makes them particularly suitable for embolic protection during endovascular procedures on or close to the heart.

18 Claims, 16 Drawing Sheets

(51) Int. Cl.
*A61M 25/10* (2013.01)
*A61B 17/22* (2006.01)

(52) U.S. Cl.
CPC .. *A61B 17/12045* (2013.01); *A61B 17/12136* (2013.01); *A61F 2/013* (2013.01); *A61M 25/10* (2013.01); *A61B 2017/22067* (2013.01); *A61B 2017/22079* (2013.01)

(56) References Cited

U.S. PATENT DOCUMENTS

| | | | |
|---|---|---|---|
| 6,051,014 | A | 4/2000 | Jang |
| 6,126,673 | A | 10/2000 | Kim et al. |
| 6,146,396 | A | 11/2000 | Kónya et al. |
| 6,287,321 | B1 | 9/2001 | Jang |
| 6,314,310 | B1 | 11/2001 | Ben-Haim et al. |
| 6,336,934 | B1 | 1/2002 | Gilson et al. |
| 6,454,799 | B1 | 9/2002 | Schreck |
| 6,499,487 | B1 | 12/2002 | McKenzie et al. |
| 6,517,559 | B1 | 2/2003 | O'Connell |
| 6,537,297 | B2 | 3/2003 | Tsugita et al. |
| 6,620,148 | B1 * | 9/2003 | Tsugita ............ 604/509 |
| 6,663,652 | B2 | 12/2003 | Daniel et al. |
| 6,719,717 | B1 | 4/2004 | Johnson et al. |
| 6,726,621 | B2 | 4/2004 | Suon et al. |
| 6,740,061 | B1 | 5/2004 | Oslund et al. |
| 6,958,074 | B2 | 10/2005 | Russell |
| 7,174,636 | B2 * | 2/2007 | Lowe ............ 29/896.62 |
| 7,303,575 | B2 | 12/2007 | Ogle |
| 7,329,278 | B2 | 2/2008 | Seguin et al. |
| 7,749,245 | B2 * | 7/2010 | Cohn ............ A61F 2/2412 606/200 |
| 7,837,702 | B2 | 11/2010 | Bates |
| 7,879,062 | B2 | 2/2011 | Galdonik et al. |
| 7,879,067 | B2 | 2/2011 | Galdonik et al. |
| 8,021,351 | B2 | 9/2011 | Boldenow et al. |
| 8,070,694 | B2 | 12/2011 | Galdonik et al. |
| 8,092,483 | B2 | 1/2012 | Galdonik et al. |
| 8,206,412 | B2 | 6/2012 | Galdonik et al. |
| 8,372,108 | B2 | 2/2013 | Lashinski |
| 2001/0012951 | A1 * | 8/2001 | Bates ............ A61F 2/013 606/200 |
| 2002/0022858 | A1 | 2/2002 | Demond et al. |
| 2002/0068015 | A1 | 6/2002 | Polaschegg et al. |
| 2002/0165573 | A1 | 11/2002 | Barbut |
| 2002/0173819 | A1 | 11/2002 | Leeflang et al. |
| 2003/0144686 | A1 | 7/2003 | Martinez et al. |
| 2004/0002730 | A1 | 1/2004 | Denison et al. |
| 2004/0243175 | A1 | 12/2004 | Don Michael |
| 2005/0015048 | A1 * | 1/2005 | Chiu et al. ............ 604/101.04 |
| 2005/0085847 | A1 | 4/2005 | Galdonik et al. |
| 2005/0137696 | A1 | 6/2005 | Salahieh et al. |
| 2005/0209631 | A1 | 9/2005 | Galdonik et al. |
| 2005/0251246 | A1 * | 11/2005 | Dubrul et al. ............ 623/1.42 |
| 2005/0277976 | A1 | 12/2005 | Galdonik et al. |
| 2006/0047301 | A1 | 3/2006 | Ogle |
| 2006/0161241 | A1 | 7/2006 | Barbut et al. |
| 2006/0200047 | A1 | 9/2006 | Galdonik et al. |
| 2007/0060944 | A1 | 3/2007 | Boldenow et al. |
| 2007/0172526 | A1 | 7/2007 | Galdonik et al. |
| 2007/0208302 | A1 | 9/2007 | Webster et al. |
| 2008/0033467 | A1 | 2/2008 | Miyamoto et al. |
| 2008/0065145 | A1 | 3/2008 | Carpenter |
| 2008/0086110 | A1 | 4/2008 | Galdonik et al. |
| 2008/0109088 | A1 | 5/2008 | Galdonik et al. |
| 2008/0172066 | A9 | 7/2008 | Galdonik et al. |
| 2009/0326575 | A1 | 12/2009 | Galdonik et al. |
| 2010/0010476 | A1 | 1/2010 | Galdonik et al. |
| 2010/0036481 | A1 * | 2/2010 | Dubrul et al. ............ 623/1.42 |
| 2010/0179583 | A1 | 7/2010 | Carpenter et al. |
| 2010/0179584 | A1 | 7/2010 | Carpenter et al. |
| 2010/0179585 | A1 | 7/2010 | Carpenter et al. |
| 2010/0179647 | A1 | 7/2010 | Carpenter et al. |
| 2010/0185231 | A1 | 7/2010 | Lashinski |
| 2010/0191276 | A1 | 7/2010 | Lashinski |
| 2010/0211095 | A1 | 8/2010 | Carpenter et al. |
| 2010/0324589 | A1 | 12/2010 | Carpenter et al. |
| 2011/0022076 | A1 | 1/2011 | Lashinski |
| 2011/0093000 | A1 | 4/2011 | Ogle et al. |
| 2011/0282379 | A1 | 11/2011 | Lee et al. |
| 2011/0313445 | A1 | 12/2011 | Galdonik et al. |
| 2012/0179195 | A1 | 7/2012 | Lashinski |

FOREIGN PATENT DOCUMENTS

| | | |
|---|---|---|
| WO | 2008/033845 A2 | 3/2008 |
| WO | 2010/081025 A1 | 7/2010 |
| WO | 2010/083527 A2 | 7/2010 |
| WO | 2010/088520 A2 | 8/2010 |
| WO | 2011/017103 A2 | 2/2011 |
| WO | 2011/034718 A2 | 3/2011 |

OTHER PUBLICATIONS

Fiber Innovative Technology: biocomponent and specialty fibers; FIT Capabilities; http://web.archive.org/web/20010217040848/http://www.fitfibers.com/capabilites.htm (Feb. 17, 2001).

Fiber Innovative Technology: biocomponent and specialty fibers; FIT Products; http://web.archive.org/web/20010408003529/http://www.fitfibers.com/product.htm.

Ghanem et al., "Risk and Fate of Cerebral Embolism after Transfemoral Aoritic Valve Implementation," J. Am. Coll. Cardiol., 55:14 (2010) 1427-1432.

International Search Report and Written Opinion for co-pending PCT application No. PCT/US13/21734 dated Mar. 26, 2013 (10 pages).

European Search Report for European application No. EP 13738839 dated Jul. 28, 2015 (6 pages).

* cited by examiner

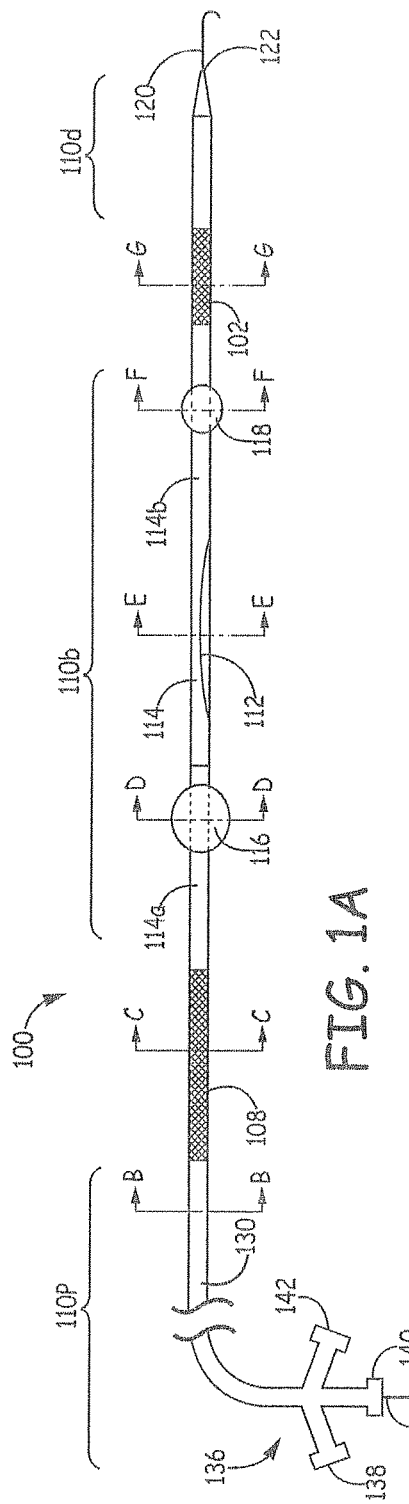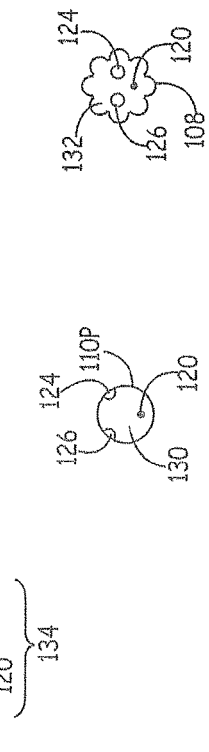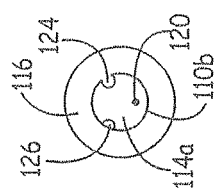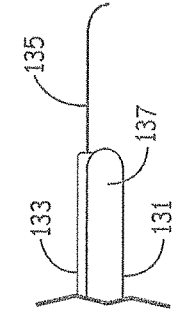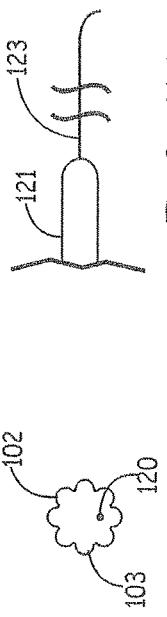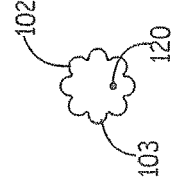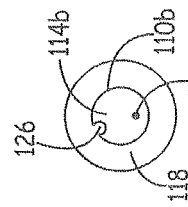

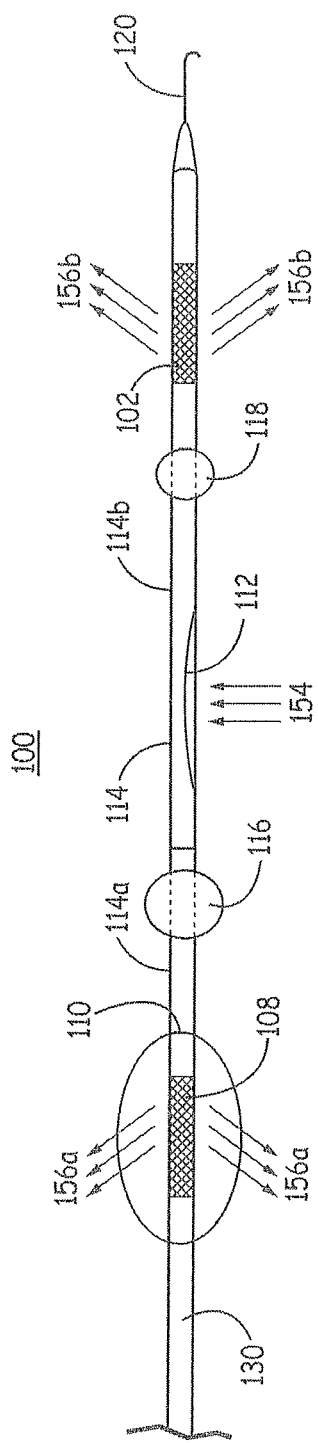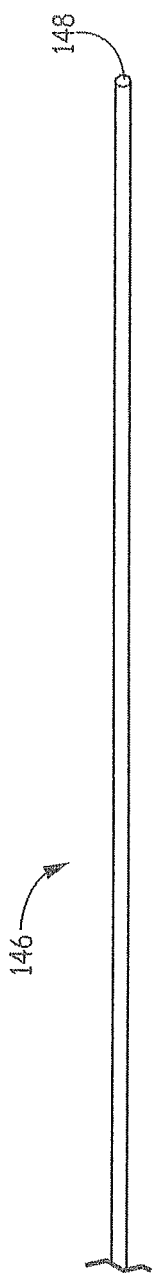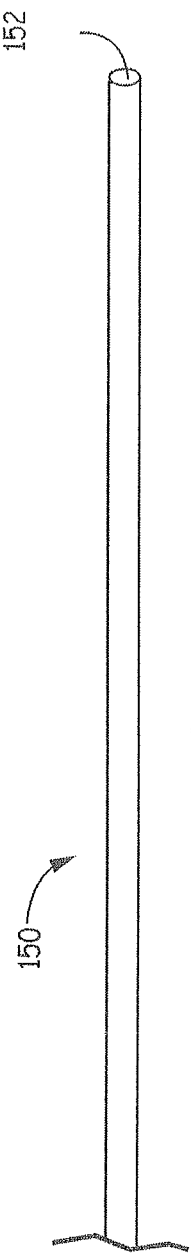
FIG. 2A
FIG. 2B
FIG. 2C

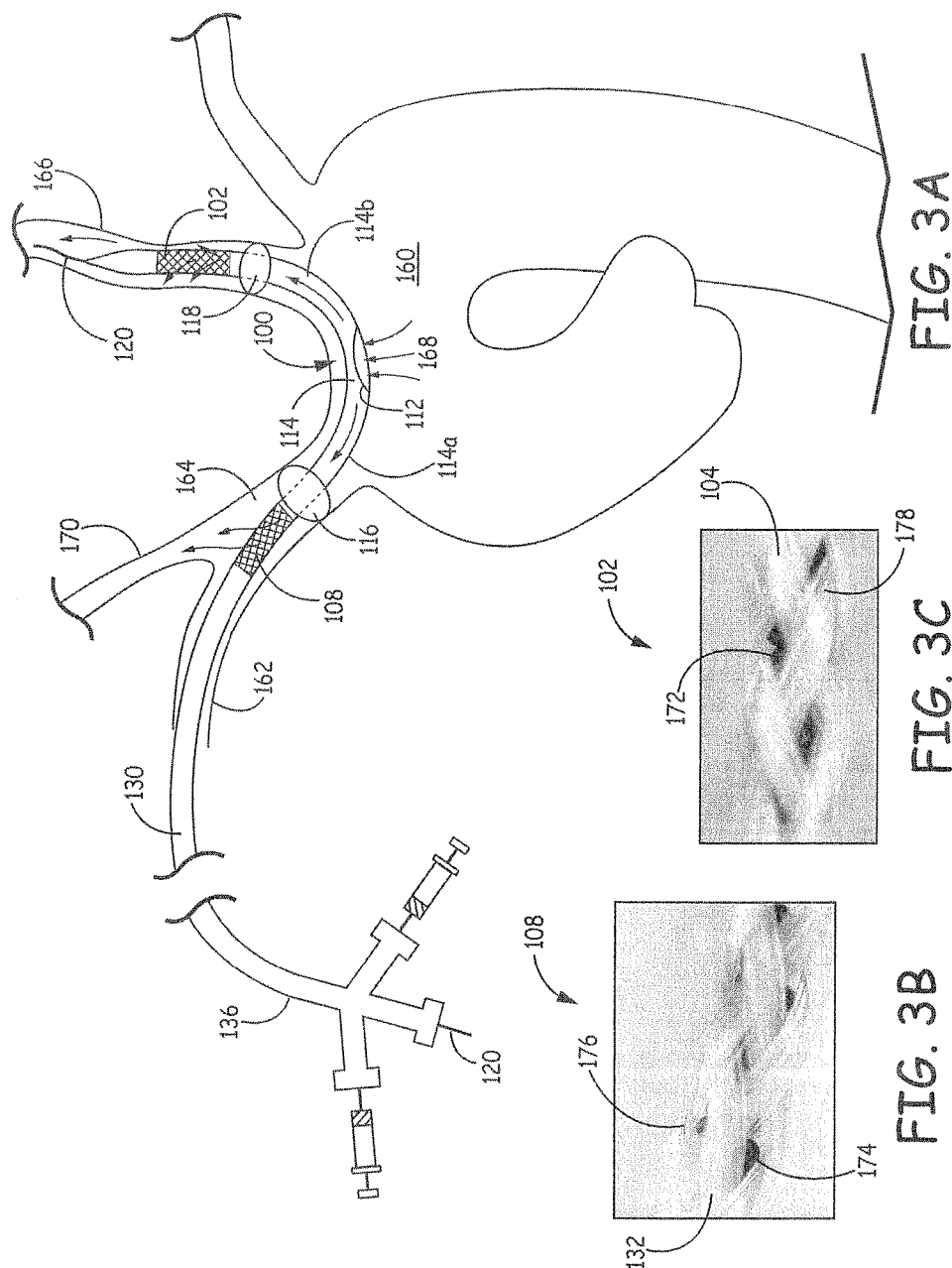

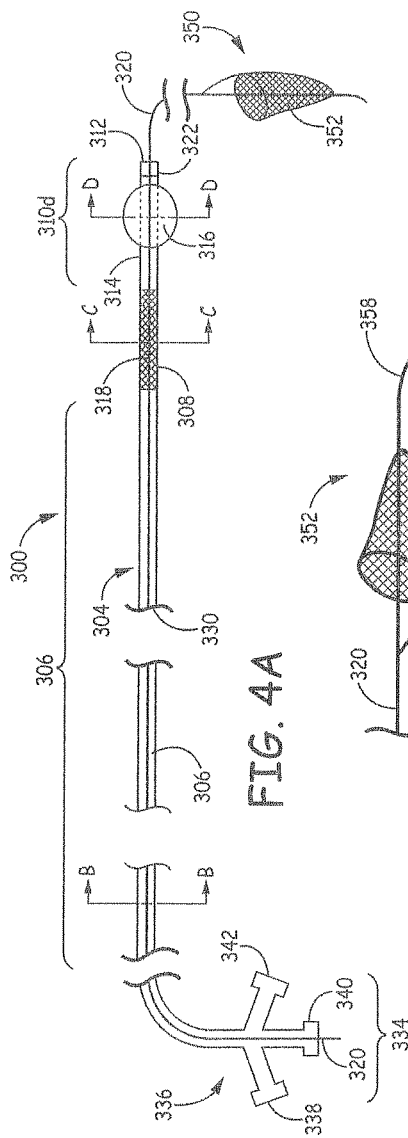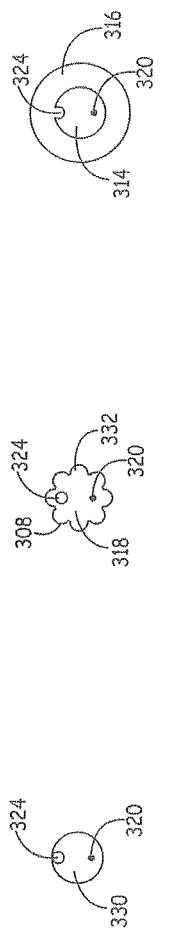

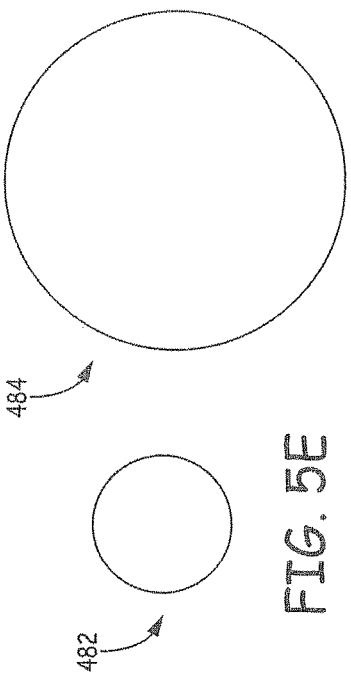
FIG. 5D
FIG. 5E
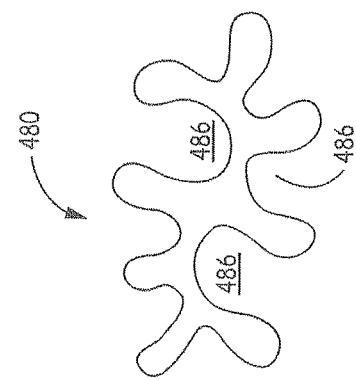
FIG. 5F
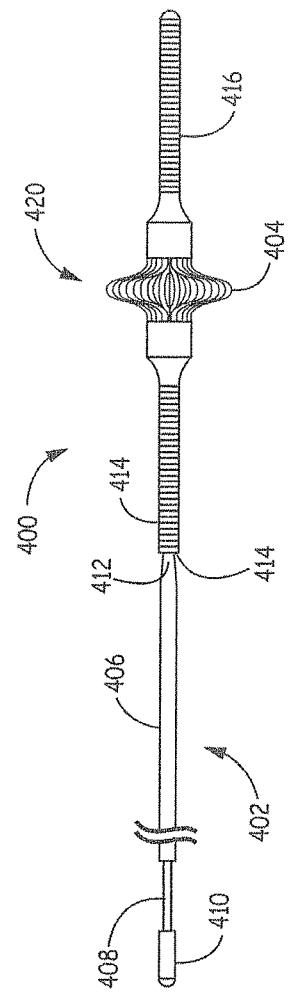
FIG. 5G

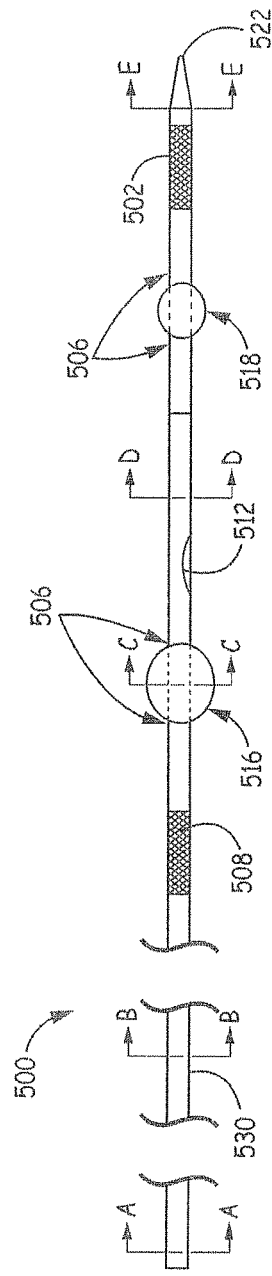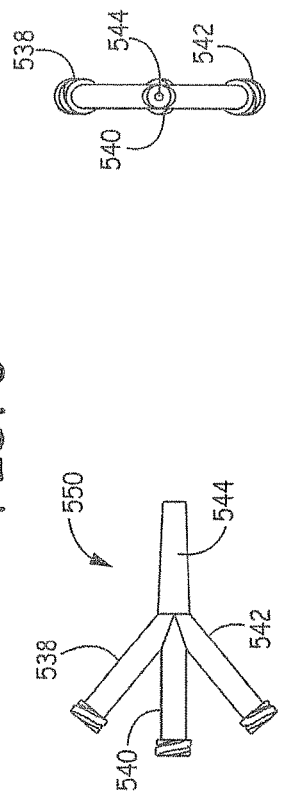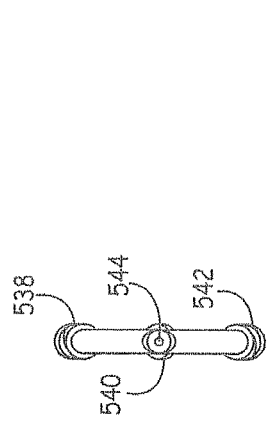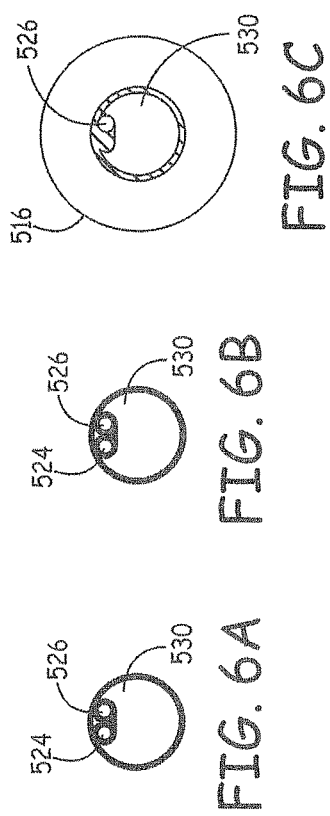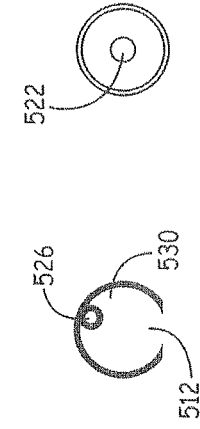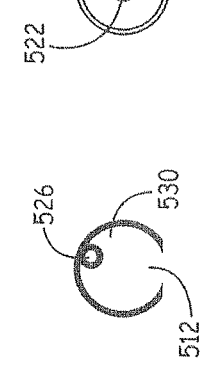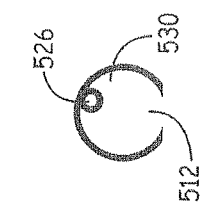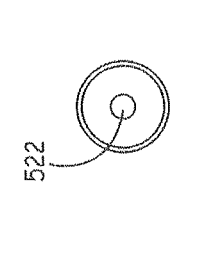

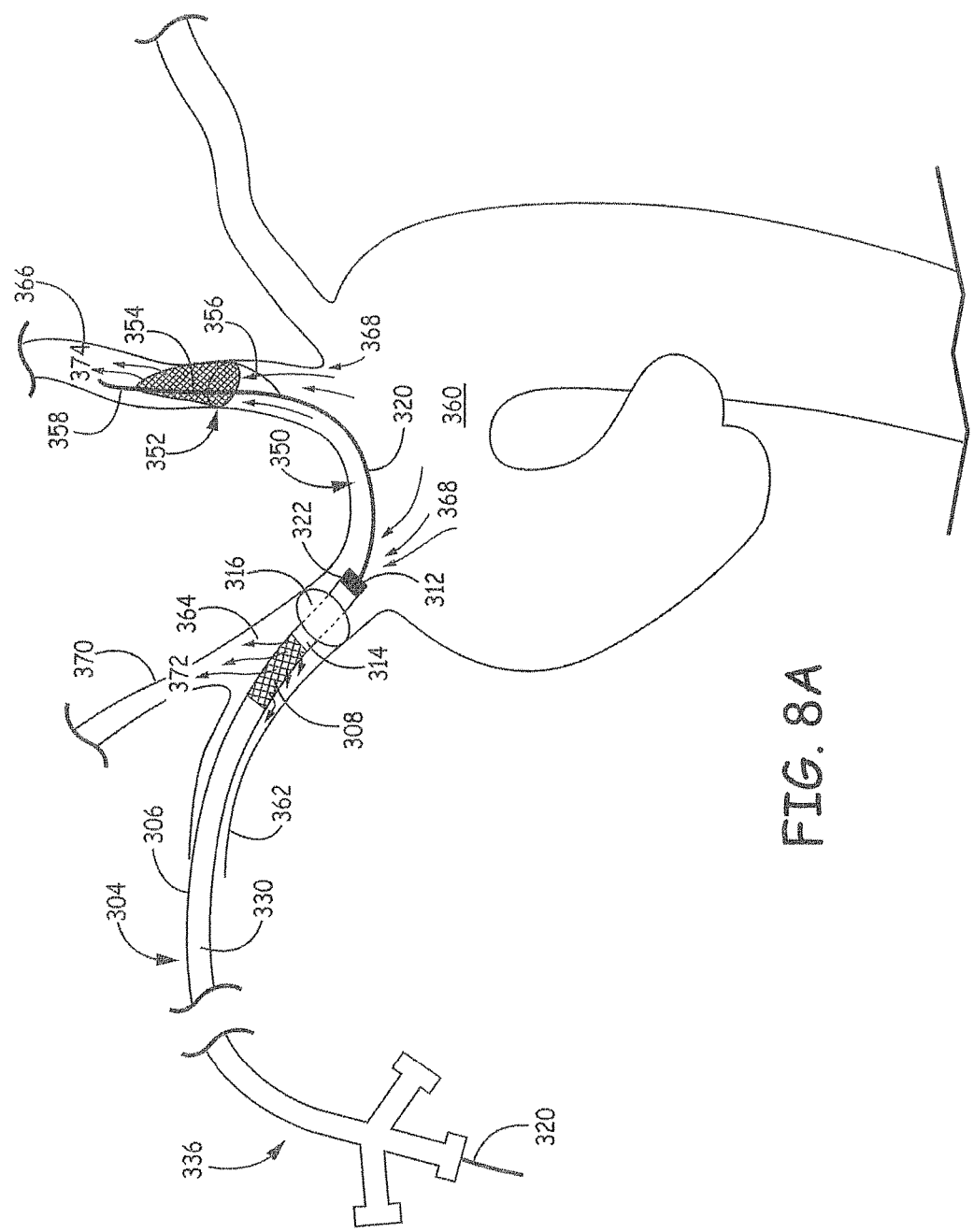

AORTIC ARCH FILTRATION SYSTEM FOR CAROTID ARTERY PROTECTION

CROSS REFERENCE TO RELATED APPLICATIONS

This application claims priority to U.S. provisional patent application 61/587,413 filed on Jan. 17, 2012 to Ganesan et al., entitled "Aortic Arch Filter Structure for Carotid Artery Protection" and U.S. provisional patent application 61/661,643 filed on Jun. 19, 2012 to Ganesan et al., entitled "Aortic Arch Filtration Catheter for Carotid Artery Protection," both of which are incorporated herein by reference.

FIELD OF THE INVENTION

The inventions, in general, are related to embolic protection devices for inhibiting emboli from entering the carotid arteries from the aorta. The inventions are further related to filtration systems with a component that extends from the brachiocephalic artery to the left carotid artery along the aortic arch to filter flow from the aorta. The invention also relates to methods for use of such filtration systems, such as during procedures on the heart that can generate emboli at the aortic arch.

BACKGROUND

Less invasive procedures can provide desirable medical results with reduced recovery time and reduced risk to the patient. Thus, many surgical procedures are performed using endoscopes or the like in percutaneous formats. A large number of less invasive procedures within the cardiovascular system are now commonly performed, such as angiograms, angioplasty procedures and stent delivery procedures.

Endovascular procedures on or in the vicinity of the heart can create a risk of emboli generation in the aorta near the heart. Other procedures on the heart may also generate emboli along the ascending aorta. Emboli in the ascending aorta can enter the carotid arteries along the aortic arch, and emboli in the coronary arteries can travel to the brain and cause a stroke. Heart valve prostheses have been successfully used to replace damaged natural heart valves that no longer perform their functions in a satisfactory way. Commercial heart valve prostheses include both mechanical valves with rigid occluders and tissue-based prostheses with flexible leaflets. These valves have been implanted surgically through the chest with the patient on cardiopulmonary bypass. Prosthetic heart valves have been developed for percutaneous or endovascular delivery, such as the Sapien™ aortic heart valve prosthesis from Edwards Lifesciences. While endovascular procedures are significantly less invasive to the patient than procedures through the chest wall, these procedures can create risk from emboli within the aortic root that can travel to the brain and cause strokes. Ghanem et al. for example discussed embolization during transcatheter aortic-valve implantation procedure in an articled in Journal of American College of Cardiology Vol. 55, No. 14, 2010, pg. 1427-1432 entitled "Risk and Fate of Cerebral Embolism After Transfemoral Aortic Valve Implantation," incorporated herein by reference.

SUMMARY OF THE INVENTION

In a first aspect, the invention pertains to a biocompatible filtration catheter. The catheter can comprise a shaft having a proximal end and a distal end with a distal opening; an integrated filter element integrated as part of a wall of the shaft at or near the distal end of the shaft, wherein the integrated filter element provides for fluid flow out from the interior of the catheter; a distal section extending in a distal orientation from the integrated filter element; an occlusive element associated with the exterior of the distal section at or near the distal end of the catheter that can extend radially outward from the exterior of and around the circumference of the shaft; and a conduit extending within the shaft from the distal end through at least the distal section to the integrated filter element to provide fluid communication between the distal opening and the integrated filter element. In some embodiments, the integrated filter element of the filtration catheter comprises interwoven fibers. The interwoven fibers of the filter element can further comprise metal filaments and/or surface capillary fibers. The integrated filter element generally has a length from about 10 mm to about 70 mm and effective pore sizes of about 50 micron to about 500 micron. The integrated filter element generally comprises approximately the same outer diameter as the shaft of the filtration catheter. In some embodiments, the occlusive element of the filtration catheter is a balloon, which has an extended configuration with a diameter suitable to occlude a human brachiocephalic artery. In some embodiments, the balloon comprises a compliant deformable material connected to an exterior surface of the distal section to provide for inflation of the balloon. The shaft of the filtration catheter can comprise a balloon lumen to provide fluid communication between a proximal port and the interior of the balloon. In one embodiment, the filtration catheter has a diameter between about 5 Fr to about 7 Fr. In some embodiments, the filtration catheter can further comprise a sheath slidably positioned over the catheter having a configuration extended in a distal direction relative to the catheter covering the integrated filter element.

In a second aspect, the invention pertains to a filtration system. The filtration system can comprise a filtration catheter described herein and a filter device that comprises a guide structure and an independent filter element supported by the guide structure. In general, the filtration catheter comprises a central lumen that is suitable for the delivery of the independent filter element mounted on the guide structure through the distal opening of the shaft. In some embodiments, the independent filter element of the filter device comprises surface capillary fibers (SCF fiber filter element) having a first configuration in a bundle with a low profile and an extended configuration with the centers of the fibers flaring outward from the guide structure. The guide structure used for SCF fiber filter element can comprise a corewire and an overtube with the corewire extending through a lumen of the overtube. The relative movement of the corewire and the overtube transitions the SCF fibers from the low profile configuration to the extended configuration. In some embodiments, the independent filter element of the filter device comprises a filter basket. The filter basket in some embodiments can comprise an opening into the filter basket oriented toward the proximal end of the guide structure. In some embodiment, the filtration system described herein further comprises an aspiration catheter with dimension providing for placement over the guide structure of the filter device and delivery through the lumen of the filtration catheter.

In a third aspect, the invention pertains to a method for providing embolic protection during an endovascular procedure on or near a patient's heart using a filtration system described herein. The filtration system comprises a filtration catheter that comprises a shaft with an inflow opening and a flow conduit, a first integrated filter element replacing a portion of the shaft and an occlusive element distal to the integrated filter element and proximal to the inflow opening with the flow conduit extending from the inflow opening to the integrated filter element. The embolic protection method comprises delivering the filtration catheter through the right subclavian artery to position the occlusive element in the brachiocephalic artery and deploying the occlusive element to redirect blood to enter the inflow opening, flow through the flow conduit, and exit as filtered flow through the first integrated filter element into the brachiocephalic artery, bypassing the occlusive element. In embodiments where the filtration catheter comprises a second integrated filter element and a second occlusive element distal to the first integrated filter element and proximal to the second integrated filter element with a distal flow conduit providing fluid communication between the inflow opening and the second integrated filter element past the second occlusive element, delivery of the catheter positions the second occlusive element within the left carotid artery, and the embolic protection method further comprises deploying the second occlusive element to redirect blood to enter the inflow opening, flow through the conduit, and exit as filtered flow through the second integrated filter element into the left carotid artery, bypassing the second occlusive element. In embodiments where the occlusive elements are balloons, the deployment of the occlusive elements comprises inflating the balloons. In some embodiments, the embolic protection method further comprises delivering a filter device with an independent filter element through a lumen of the filtration catheter into the left carotid artery and deploying the independent filter element to filter blood flowing into the left carotid artery. In general, the flow rate of filtered blood flow into the right carotid artery is at least about 50% of the natural blood flow. The positioning of occlusive element can be assisted with x-ray visualization. In some embodiments, the embolic protection method further comprises applying aspiration to the integrated filter element through a main lumen of the filtration catheter to remove the emboli trapped inside the integrated filter element. The method in general further comprises collapsing the occlusive element followed by removing the filtration catheter from the patient. The embolic protection method can further comprises performing an endovascular procedure on the heart, delivering a heart valve delivery catheter through the descending aorta or the subclavian artery to the heart to effect at least a step related to removal of a heart valve or the placement of a prosthetic heart valve, or performing a surgical procedure on the heart while the filtration system is filtering flow into the carotid arteries. In one embodiment, the endovascular procedure comprises replacement of the aortic valve while the filtration system is filtering flow into the carotid arteries.

In a fourth aspect, the invention pertains to a biocompatible filtration catheter that can comprise a proximal section; a proximal filter element integrated as part of a wall of the catheter at or near the distal end of the proximal section; a bridge section extending in a distal direction relative to the proximal filter and comprising a proximal conduit, a distal conduit and an inflow opening between the proximal conduit and the distal conduit; a distal filter element integrated as part of the wall of the catheter at or near the distal end of the distal conduit; a distal section extending in a distal orientation from the distal filter element; a proximal occlusive element associated with the exterior of the proximal conduit between the proximal filter element and the inflow opening; and a distal occlusive element associated with the exterior of the distal conduit between the distal filter element and the inflow opening. The inflow opening is between the distal filter element and the proximal filter element of the catheter. The proximal conduit of the catheter provides fluid communication between the proximal filter element and the inflow opening and the distal conduit of the catheter provides fluid communication between the distal filter element and the inflow opening. The occlusive elements of the filtration catheter can extend radially outward from the exterior of the conduits around the circumference of the catheter. The integrated filter elements of the filtration catheter provide fluid communication between the inflow opening and the exterior of the catheter through the conduits. In some embodiments, the filtration catheter further comprises a distal guide port at or near the distal end of the distal section. In some embodiments, the distal section of the filtration catheter comprises a closed tubing section. The filtration catheter can have a diameter between about 5 Fr to about 7 Fr. The integrated filter elements of the filtration catheter comprise approximately the same diameter as the catheter. In some embodiments, the occlusive elements of the filtration catheter are compliant balloons. The filtration catheter can comprise at least one balloon lumen inside the catheter to inflate the balloons. In some embodiments, the integrated filter elements of the filtration catheter comprise interwoven fibers. The interwoven fibers of the filtration catheter can further comprise metal filaments and or surface capillary fibers. In some embodiments, the proximal filter element of the filtration catheter has a length from about 10 mm to about 80 mm while the distal filter element has a length from about 5 mm to about 30 mm. The filter elements of the filtration catheter can have pore sizes of about 50 micron to about 500 micron. The distance between the occlusive elements of the filtration catheter can be about 30 mm to about 120 mm. In some embodiments, the filtration catheter can further comprise sheath slidably positioned over the catheter having a configuration extended in a distal direction relative to the catheter covering occlusive elements in an unextended configuration.

In a fifth aspect, the invention pertains to a biocompatible filtration catheter that can comprise a proximal section; a proximal filter element; a bridge section extending in a distal direction relative to the proximal section and comprising a proximal conduit, a distal conduit and an inflow opening; a distal filter element; a distal section extending in a distal orientation relative to the distal filter element and comprising a guide port at the distal end; a proximal occlusive element associated with the exterior of the proximal conduit; and a distal occlusive element associated with the exterior of the distal conduit. The inflow opening of the filtration catheter is between the distal filter element and the proximal filter element. The proximal conduit of the filtration catheter provides fluid communication between the proximal filter element and the inflow opening, and the distal conduit of the filtration catheter provides fluid communication between the distal filter element and the inflow opening. The occlusive elements of the filtration catheter can extend radially outward from the exterior of the conduit around the circumference of the catheter. The conduits of the filtration catheter provide fluid communication between the inflow opening and the exterior of the catheter through the filter elements.

In a sixth aspect, the invention pertains to a method for restricting emboli from entering the carotid arteries in a patient using a filtration catheter that comprises a proximal section, a distal filter element, a proximal filter element at or near the distal end of the proximal section, a bridge section connecting the proximal filter element and the distal filter element and comprising a proximal conduit and a distal conduit, and an inflow opening between the distal filter element and the proximal filter element. The embolic protection method comprises delivering a guidewire from the right subclavian artery, through the brachiocephalic artery, along the aortic arch to the left carotid artery; tracking the filtration catheter over the guidewire to position the distal occlusive element inside the left carotid artery, the proximal occlusive element inside the brachiocephalic artery, and the inflow opening inside the aortic arch; and expanding the proximal occlusive element and the distal occlusive element to make sealing engagements with the walls of the brachiocephalic artery and the left carotid artery respectively to inhibit direct blood flow from entering into respective arteries while redirecting the blood flow to enter the inflow opening, to flow through the conduits and then to exit the filter elements to provide filtered blood flow into the left carotid artery and the right carotid artery from the aorta. The flow rate of filtered blood flow is at least about 50% of the natural blood flow in respective arteries. In some embodiments, the flow rate of filtered blood flow is at least about 70% of the natural blood flow in respective arteries. The positioning of occlusive elements can be assisted with x-ray visualization. In some embodiments, the embolic protection method further comprises applying aspiration to the filter elements through a main lumen of the filtration catheter to remove the emboli trapped inside the filter elements. The method further comprises collapsing the occlusive elements followed by removing the filtration catheter from the patient.

BRIEF DESCRIPTION OF THE DRAWINGS

FIG. 1A is a schematic diagram of a filtration catheter according to one embodiment of the invention.

FIGS. 1B-1G are sectional views taken at respective different lines of filtration catheter of FIG. 1A.

FIGS. 1H and 1I are fragmentary side views of alternative embodiments of the distal section of the filtration catheter of FIG. 1A.

FIG. 2A is a schematic diagram of the filtration catheter of FIG. 1A with arrows illustrating blood flow through the conduit and the integrated filter elements.

FIG. 2B is a side view of an obturator that can be used to facilitate delivery of the filtration catheter of FIG. 1A.

FIG. 2C is a side view of a sheath that can be used to facilitate retrieval of the filtration catheter of FIG. 1A.

FIG. 3A is a schematic diagram illustrating the filtration catheter of FIG. 1A placed inside an aortic arch by way of the right subclavian artery.

FIGS. 3B and 3C are a set of photographs of a specific embodiment of the integrated filter elements with emboli trapped inside the fiber braids of the filter elements.

FIG. 4A is a schematic diagram of a second type of filtration system according to one embodiment of the invention with a filter device delivered through the lumen of a second type of filtration catheter.

FIGS. 4B-4D are sectional views taken at respective different lines of filtration system of FIG. 4A.

FIG. 4E is an enlarged fragmentary side view of the independent filter element of the filtration system of FIG. 4A showing the detailed features of the filter basket.

FIG. 5D is a schematic sectional view of an embodiment of a surface capillary fiber.

FIGS. 5E and 5F are schematic sectional views of two contrasting round fibers.

FIG. 5G is a fragmentary side view of an alternative embodiment of a filter device that can be delivered through the filtration catheter of FIG. 4A.

FIG. 6 is a fragmentary view of a specific design of a filtration catheter with two integrated filtration elements.

FIGS. 6A-6E are a set of sectional views taken along respective lines of filtration catheter of FIG. 6.

FIG. 6F is a fragmentary side view of the proximal fittings of the filtration catheter of FIG. 6.

FIG. 6G is a plan view of the proximal fittings of FIG. 6F looking in a proximal direction along the catheter axis from the fragmentary view of FIG. 6F.

FIG. 8A is a schematic diagram illustrating the filtration system of FIG. 4A placed inside an aortic arch by way of the right subclavian artery.

DETAILED DESCRIPTION

Figure 3D:
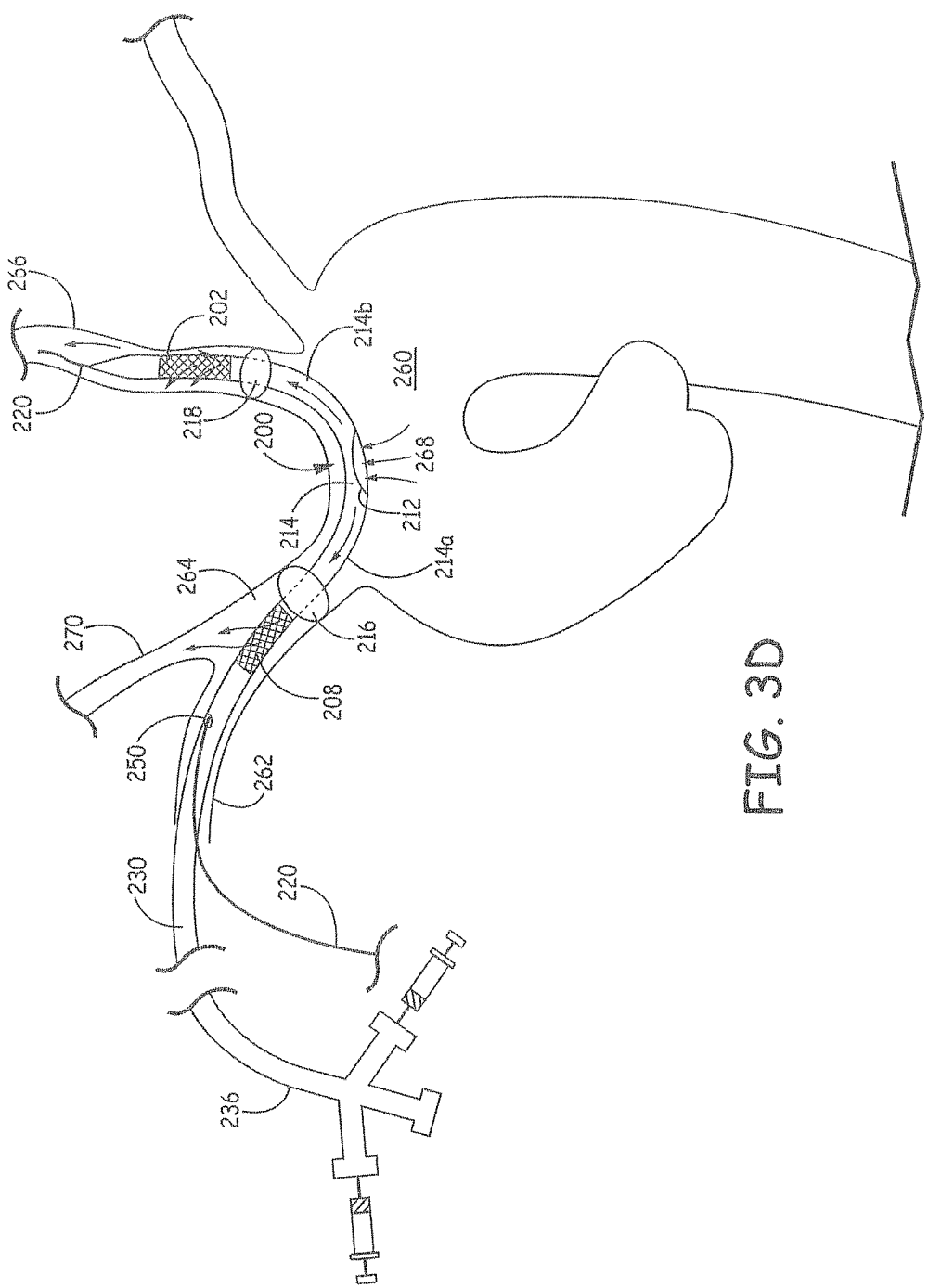
FIG. 3D is a schematic diagram illustrating a rapid exchange version of the filtration catheter of FIG. 1A placed inside an aortic arch by way of the right subclavian artery.

The filtration systems described herein provides protection to the left carotid artery and the brachiocephalic artery, which leads to the right carotid artery, against embolization from the aortic arch during procedures, such as transcatheter aortic-valve implantation (TAVI), aortic heart valve repairs and other procedure on or near the heart. Improved embolic protection devices are described herein with a convenient construction that has two filters configured for easy delivery and removal while restricting emboli from entering the carotid arteries during heart valve replacement procedures and other endovascular procedures that have a risk of providing emboli into the aortic arch. Two general system designs are presented, and both systems are designed to provide filtration of flow from the aorta into both the left carotid artery and right carotid artery while providing little obstruction along the aortic arch.

Filtration systems are described that provide for introduction of a distal end of the filtering catheter into the brachiocephalic artery with a portion of the system configured for extending from the brachiocephalic artery to the left carotid artery such that following deployment, flow from the aorta can be filtered into both carotid arteries. A first filtration system has a catheter that can span from the entrance into the brachiocephalic artery along the aortic arch to the left carotid artery. The catheter of this first type of system has an inflow opening into the interior lumen to provide internal flow into both a distal direction and a proximal direction relative to the inflow opening and respective filters built into the wall of the catheter to provide filtered flow. With the use of appropriately positioned balloons or other flow obstructers along the exterior of the catheter, filtered flow can be provided to the left carotid artery and into the brachiocephalic artery, for flow into the right carotid artery. In the second filtration system, a filtration catheter is designed for positioning the distal section in the brachiocephalic artery, and the filtration catheter comprises a filter integrated with the catheter wall along with a balloon or other flow obstruction device on the catheter outer surface to provide filtered flow from a distal opening out through the filter at a position proximal to the obstruction device within the brachiocephalic artery. For the second filtration system, a filter associated with a guide structure can be extended from the distal opening of the catheter for placement of the filter into the left carotid artery. Thus, each of the two filtration systems described herein comprise a filtration catheter. For consistency and ease of the discussion, the type of filtration catheter of the first type of filtration system is referred to as the first filtration catheter while the type of filtration catheter of the second type of filtration system is referred to as the second filtration catheter. As is conventional in the art, in a percutaneous or endovascular procedures, a distal direction refers to a position further from the insertion point into the body along the path of the device, and a proximal direction refers to a position closer to the insertion point.

The embolic protection systems comprise a filtration catheter having either one or two occlusive elements to block unfiltered blood flow into one or both carotid arteries. The first filtration catheter provides a conduit placed inside the aortic arch with filter elements placed along the conduit to trap the emboli before the blood exits the conduit and enters the carotid arteries as well as the brachiocephalic artery. In particular, the filter elements generally are incorporated into the structural wall of a filtration catheter to provide filtered flow past the respective occlusive elements. In the second system, just one filter element is provided through incorporation into the structural wall of the filtration catheter, and another filter connected to a guide structure is used to provide filtration for the left carotid artery following placement from the brachiocephalic artery along the aortic arch. The filtration catheters provide desirable delivery into the appropriate locations in the vessels as well as convenient retrieval after completion of the procedure with a low risk of releasing emboli into the carotid arteries during removal of the catheter. Each filtration system design provides particular advantages. With the first filtration system, because the filter elements are stationary relative to the other elements of the catheter, the filtration catheter can be quickly removed with little risk of releasing the emboli at the end of the procedure. With the second filtration system, the delivery of the filter into the left carotid artery can be accomplished with only a guide structure extending across the aortic arch.

The filtration systems are designed for delivery through the right subclavian artery with a component traversing a portion of the aortic arch from the brachiocephalic artery to reach the left carotid artery. In the first system design, only the body of the filtration catheter, which would occupy a small volume relative to the other endovascular devices used in the aorta, resides along the aortic arch during the operational process. For the second system design, only a guide structure or the like, which would occupy a very small volume, resides along the aortic arch during the operational process. Both systems involve deployment of a first occlusive element in the brachiocephalic artery. Upon deployment of a second occlusive element in the left carotid artery for the first system or the deployment of a filter structure in the left carotid artery for the second system, the filtration system provides simultaneous filtration of blood into right carotid artery and into the left carotid artery. Thus, the practical filtration systems described herein do not significantly interfere with blood flow or other devices in the aortic arch, provides effective embolic protections to the carotid arteries, and can be quickly removed without significant risk at the end of a procedure. In some embodiments, the catheter may include one or more balloons as occlusive elements to be used in conjunction with filters that effectively protect the carotid arteries by capturing/deflecting clots from the heart arteries and/or valves. The balloon in general can be soft and compliant to secure the position of the catheter and to re-direct blood in the vessel to flow through a filter element integrated with a catheter wall. In a specific commercial design, the filtration catheter may be delivered via a 6-7 French (Fr, 1 Fr=(⅓) mm) introducer sheath through a right side upper extremity access.

In general, the filtration catheter of either filtration system can be tracked through a brachial or radial approach without kink or damage during delivery. The filtration catheter for either filtration system additionally can be designed to withstand normal torque forces during a relevant medical procedure. The filtration catheter in general can be soft and atraumatic to blood vessels. The concept of delivering filter elements through the right subclavian artery into the right carotid artery or brachiocephalic artery and the left carotid artery so a portion of the delivery or guide structure spans between the brachiocephalic artery and the left carotid artery inside the aortic arch has been described in published U.S. Pat. No. 8,206,412 to Galdonik et al., entitled "Embolic Protection During Percutaneous Heart Valve Replacement and Similar Procedures," incorporated herein by reference. The filtration catheters described herein integrate filter element(s) directly on the shaft of a catheter to provide filter element(s) that does not require extending and collapsing procedures, thus significantly simplify the delivery and retrieval procedures while providing desired retention and removal of the emboli. Also, the filter designs integrated into the catheter wall as described herein can provide for desired flow levels through the filter element(s) with practical filter designs within the size constraints imposed by the vessels sizes.

With respect to the first type of filtration system design, the filtration catheter comprises a distal section, a distal filter element, a bridge section with two occlusive elements and an inflow opening, a proximal filter element and a proximal section in which adjacent elements are appropriately attached to form an integrated filtration catheter. In some embodiments, the filtration catheter may have a main lumen that extends through the entire length of the catheter, and the main lumen can be used as a guide lumen if the lumen has a distal guide port. The bridge section of the filtration catheter is designed to have a proximal conduit and a distal conduit that can be part of the main lumen to provide fluid communication from the inflow opening to the proximal filter element and the distal filter elements respectively. The filtration catheter for the second filtration system is an alternative catheter design comprising a flow control section with a single occlusive element, a filter element proximal to the occlusive element and a proximal section.

With respect to the first type of filtration catheter structure, the distal section of the filtration catheter is attached at or near its proximal end with the distal filter element. The distal section in general is designed to restrict unfiltered flow from exiting the interior lumen of the catheter. In general, the filtration catheter can be designed to ride over a guide structure, such as a guide wire, such as through the main lumen for delivery of the catheter into a desired location for use. In some embodiments, the distal section can have a guide port at the distal tip. The guide port, if present, should have a small clearance over a corresponding guide structure such that little if any unfiltered blood can flow from the guide port, although a separate guide lumen can be used if desired to separate the guide structure from the blood flow or alternatively a fixed guide structure can be connected at the distal end of the distal section. If the filtration catheter is designed to ride over a guide structure, the main lumen for the guide structure can extend from the distal section to the proximal section of the catheter, with the distal portion of the main lumen modified to restrict unfiltered blood flow through the distal end of the catheter. In alternative embodiments, a coil or guide wire structure can extend from the distal end of the distal section to facilitate delivery of the filtration catheter.

The second type of filtration catheter design does not have a bridging section since the catheter is not intended to bridge the aortic arch, and the flow control section of this catheter can be considered to replace the bridge section or to involve a truncated portion of the bridge section. The flow control section of the second type of filtration catheter design generally has a distal opening, which can have a diameter approximately the size of the catheter inner lumen. For both type of general filtration catheter designs, appropriate radiopaque markers can be incorporated into the filtration catheter to assist in the placement of the catheter into patient.

The second type of filtration catheter has a single integrated filter that is positioned for use to filter blood flowing into the brachiocephalic artery for further flow into the right carotid artery. Also, a single occlusive element is mounted near the distal end of the second type of filtration catheter such that the deployed occlusive element directs flow into the distal opening and out through the integrated filter element. An independent filter, generally mounted on a guide structure can be delivered through the lumen of the filtration catheter and out through the distal opening, bypassing the occlusive element. The independent filter can be directed along the aortic arch for placement within the left carotid artery to filter flow from the aorta into the left carotid artery.

An integrated filter element in the filtration catheters is generally designed as a porous tubular section that essentially replaces a segment of the catheter with a filtering porous structure. The length of the filter element along the longitudinal axis of the filtration catheter can be selected to provide the desired degree of flow and filtration capacity. For embodiments with two tubular filtration elements, e.g., a first type of filtration catheter, the tubular filter elements may or may not have the same dimensions as each other. While the tubular filter element can generally be formed from any porous material, such as a membrane with appropriately selected holes drilled through the material. In some embodiments, the filter element can be formed from woven bundles of fibers with or without additional components. In general, the fibers can be polymer fibers, metal wires or combinations thereof. In particular, bundles of polymer surface capillary fibers have been found to provide desired filtration properties while helping to maintain desired flow through the filter structure. In some embodiments, the fiber bundles with surface capillary fibers can further comprise different polymer fibers and/or metal wires, such as Nitinol wires, to provide additional structural stability to the filter elements. The weave of the filter elements can be formed to provide desired degree of filtration with respect to capture of emboli with desired size ranges while in some embodiments maintaining at least 50% of normal blood flow.

Filtration catheters with filter elements placed within the catheter lumen to provide filtered flow through a port in the catheter wall are described in U.S. Pat. No. 8,206,412 to Galdonik et al., entitled "Embolic Protection During Percutaneous Heart Valve Replacement and Similar Procedures," incorporated herein by reference. In contrast, the integrated filters of the improved filtration catheters described herein provide for improved flow of filtered blood without obstructing the inner lumen to allow for the passage of an independent filter, suction catheters, sheaths or the like to facilitate the procedure. In particular, the second type of filtration system described herein advantageously uses the open lumen within the filtration catheter for the delivery of the second independent filter for placement in the left carotid artery. For the sake of clarity, a reference to a carotid artery herein can be to the common carotid artery and/or to the interior carotid artery that supplies blood to the brain.

With respect to the first type of filtration catheter, the bridge section of the filtration catheter is generally designed for placement spanning a segment along the aortic arch. Within the catheter structure, the bridge section is connected between the distal filter element and the proximal filter element. The bridge section comprises an inflow opening to provide for flow of blood from the aortic arch to the filter elements within a conduit or lumen extending through the bridge section. The size of the inflow opening can balance the mechanical strength and flexibility of the bridge section while providing good flow through the filter elements to the carotid arteries. The bridge section further comprises a proximal conduit and a distal conduit relative to the inflow opening that respectively provide flow to the interior of the proximal filter and the distal filter. Thus, the inflow opening provides flow access through the bridge section to the interior of the proximal filter element and the distal filter element, and the inflow opening can comprise a plurality of distinct openings to provide this inflow function. Similarly, if the bridge section has sufficient mechanical strength, a significant portion of the catheter wall can be opened as inflow opening to provide the flow into the proximal conduit and the distal conduit.

The bridge section of the first type of filtration catheter also comprises a proximal occlusive element and a distal occlusive element. The proximal occlusive element is associated with exterior of filtration catheter along the proximal conduit, and the distal occlusive element is associated with exterior of filtration catheter along the distal conduit. While one or both occlusive elements can comprise a mechanical occluder or the like, balloons as convenient occlusive elements can be effectively expanded and deflated at appropriate times in the procedure. One or two balloon lumens can be used to supply fluid to inflate the balloons from the proximal portion of the filtration catheter exterior to the patient. If a single balloon lumen is used, the balloons are inflated and deflated roughly simultaneously although the flow can be designed for the balloons to roughly inflate in series, while two balloon lumens provide for independent control of inflation and deflation of the balloons. The balloons may not have the same sizes as each other since the balloon configured for deployment in the brachiocephalic artery may have a larger size than the balloon configured for deployment in the left carotid artery. The flow control section of the second type of filtration catheter has a single occlusive element corresponding to the proximal occlusive element of the bridge section of the first type of filtration catheter and can be formed with the similar structures described above in this paragraph with appropriate simplifications associated with having only a single occlusive element.

With respect to the first type of filtration catheter, conduits of the bridge section extend inside the filtration catheter and past the occlusive elements relative to the inflow opening and connect to the respective tubular filter elements such that flow redirected by the occlusive elements flows into the inflow opening, past the occlusive elements through the internal conduit, and exits through the filter elements to reenter into the blood vessels. The flow control section of the second type of filtration catheter similarly has a conduit extending past the occlusive element such that flow redirected by the occlusive element flows into the distal opening of the catheter, past the occlusive element through the conduit, and exits through the integrated filter element to reenter into the blood vessel.

In some embodiments, the catheter body can be formed from polymer and be integrated with the filter element(s), for example, using an adhesive bond, a mechanical fastener, heat bonding, polymer reflow to embed the edge of the filter element, or a combination thereof. In general, the filtration catheters and the joints of the catheter are sufficiently strong to withstand normal tensile loads during the procedure.

The proximal section of either type of filtration catheters is connected to the proximal filter element to form an integrated structure. The proximal section is generally relatively long with a proximal end of the proximal section designed to extend from the patient during the procedure, and the proximal end has appropriate fittings, as described further below, to provide for performing the procedure. In some embodiments, the filtration catheter is designed for over-the-wire delivery in which the proximal section comprises a tubular shaft extending from the proximal filter with a length suitable to extend from the patient after delivery. As noted above, for embodiments with balloon occlusive elements, one or two balloon lumen can extend from the balloons through the proximal section to appropriate fittings at or near the proximal end of the proximal section. A main lumen or a guide lumen can provide for a guide structure extending approximately the length of the device. In alternative embodiments, the filtration catheter can be configured for a rapid exchange of a guide structure through a guide port on the filtration catheter so that the guide structure does not extend through the most or all of the length of the proximal section. In some embodiments, a loading tool can be used for loading the guide structure through the guide port, for example, as described in U.S. Pat. No. 8,021,351 to Boldenow et al., entitled "Tracking Aspiration Catheter," incorporated herein by reference. In some embodiments for the first type of filtration catheter, a guidewire lumen can extend along the catheter shaft from a distal guide port at or close to the distal end of the distal occlusive element to a rapid exchange guide port proximal to the proximal filter element. The proximal end of the proximal section can comprise appropriate handles or fittings, such as Luer fittings, hemostatic valves and the like, to account for the exit of a guide structure, connection to devices, such as syringes, to provide for inflation or deflation of balloon, or other connections, as desired.

In use, either type of the filtration catheters can be delivered into an artery in the patient's right arm, for example, using conventional endovascular procedures, introducer, hemostatic fittings and the like. The filtration catheter is guided with the distal end of the catheter into the brachiocephalic artery. In general, the first type of filtration catheter is long enough to reach left carotid artery from the insertion point in the patient's right arm. For the first type of filtration catheter, a separate guide structure or a distal coil or wire tip can be guided along the portion of the aortic arch between the brachiocephalic artery and the left carotid artery to enter the left carotid artery. If a separate guide structure is used, the first type of filtration catheter can then be tracked over the guide structure to place the distal occlusive element within the left carotid artery. With proper placement of the first type of filtration catheter, the distal occlusive element is within the left carotid artery, the proximal occlusive element is within the brachiocephalic artery and the inflow opening is inside the aortic arch. With proper placement of the second type of filtration catheter, the occlusive element is within the brachiocephalic artery, with the distal opening close to the entrance of artery to aortic arch. The occlusive element(s) can be deployed with the placement of the device verified, generally with x-ray techniques. Soft, compliant balloon(s) can be used as occlusive element(s) to secure the position of the catheter as well as to re-direct flow in the vessel through the filter element(s). For the first type of filtration catheter, the occlusive elements can be deployed simultaneously or sequentially.

Once properly placed, the second type of filtration catheter can be used to deliver another embolic protection filter device such as commercially available FIBERNET®, SPIDER®, or FILTERWIRE® to the left carotid artery. In particular, the independent filter is generally tracked out from the distal opening of the second type of filtration catheter on or over a guide structure. The guide structure is guided to the left carotid artery so that the independent filter can be deployed to filter flow into the left carotid artery. In particular, a FIBERNET® filter has a convenient low profile and delivery on an associated guide structure.

With the selected filtration system deployed, a procedure, such as a heart valve replacement, can be performed on the heart that creates a risk of emboli generation in the aortic arch. Deployment of the first type of filtration catheter generally comprises extension of the two occlusive elements respectively in the left carotid artery and the brachiocephalic artery to redirect flow into the two integrated filters. Deployment of the second type of filter element comprises extension of the independent filter element in the left carotid artery and the extension of the single occlusive element in the brachiocephalic artery to deflect flow through the integrated filter element to provide for filtered flow into the brachiocephalic artery. After completing the procedure and the risk of emboli generation has decreased to appropriate levels, the occlusive element(s) can be collapsed to an appropriate configuration, and the filtration catheter can be removed from the patient along with an independent filter element if applicable. In some embodiments, aspiration maybe used to remove the emboli trapped inside the filter element(s) at the time of and/or prior to the recovery of the filtration catheter from the patient.

In some embodiments, it may be desirable to use an obturator to facilitate the delivery of the filtration catheter. The obturator can be extended through the main lumen and through the conduits of the bridge sections to provide internal mechanical support to the filter element(s) as well as to the inflow opening of the bridge section in the case of the first type of filtration catheter. Alternatively, an external sheath may be used to cover the filter element(s) including the bridge section in the case of the first type of filtration catheter during delivery and/or retrieval processes. In embodiments when suction is used for the first type of filter element, a sheath may be used to cover the inflow opening to help transmit the suction out through the distal filter element.

In general, the filtration catheter disclosed herein provides effective filtration with insured apposition of the catheter during the procedure. The filtration catheter provides little interference in the aorta and additionally accommodates various aortic arch anatomies. Simple operation procedure is required to operate the filtration catheter with essentially no recovery step involved in some embodiments.

Filtration Systems and Catheter Structure

A first type of filtration system is designed such that a single filtration catheter structure can be used to deliver two filters from a brachiocephalic approach with a bridge section of the catheter spanning the aortic arch. The first type of filtration system comprises a first type of filtration catheter as its core component that is used along with suitable fittings, any selected optional delivery components and/or recovery components, components to provide for deployment of occlusive elements and the like. Occlusive elements of the first type of filtration catheter are positioned to block the flow of unfiltered blood from the aortic arch into the left carotid artery as well as into the brachiocephalic artery from which emboli could flow into the right carotid artery. As noted above, an opening into the catheter at the bridge section of the first type of filtration catheter provides for flow into the interior of the catheter for flow from the aorta in both a distal direction and proximal direction relative to the opening. Filtered flow can exit the catheter past the respective occlusive elements through a proximal filter and a distal filter, both of which are formed as a portion of the catheter wall. Desirable flow characteristics can be obtained for filtered flow beyond the occlusive elements in the first type of filtration catheter.

A second type of filtration system is designed such that a catheter structure can be used to deliver an filter element that is integrated on the catheter into a brachiocephalic artery while a guide structure of an independent filter device is deployed extending from a distal opening of the catheter structure and spanning the aortic arch to the left carotid artery. In the case of the second type of filtration catheter, an occlusive element is positioned to block the flow of unfiltered blood from the aortic arch into the brachiocephalic artery from which emboli could flow into the right carotid artery. The distal opening of filtration catheter allows blood from the aorta flow into the interior of the catheter. Filtered flow can exit the catheter past the occlusive element through the integrated filter element that is formed as a portion of the catheter wall, while the independent filter element of the filtration system from the filter device filters the blood flows into the left carotid artery. Desirable flow characteristics can be obtained for filtered flow in both right and left carotid arteries of the second type of filtration system. The second type of filtration system may also comprise fittings, optional delivery components and/or recovery components, components to facilitate deployment of the occlusive element and other desired components suitable to facilitate the procedure.

First Type of Filtration Catheter

Referring to FIGS. 1A-1I, a filtration catheter 100 is illustrated to exemplify the features of the first type of filtration catheter. FIG. 1A is a fragmentary side view of the filtration catheter 100 with a proximal portion 136 and proximal end 134. Enlarged cross sectional views along the B-B, C-C, D-D, E-E, F-F, and G-G lines of filtration catheter 100 are illustrated in FIGS. 1B-1G respectively. As shown in FIG. 1A, filtration catheter 100 comprises a distal section 110d, a distal integrated filter element 102, a proximal section 110p, a proximal integrated filter element 108, a bridge section 110b between the two filter elements that comprises an inflow opening 112 on the shaft, a conduit 114 that comprises a proximal conduit 114a that provides fluid communication between the proximal filter element 108 and the inflow opening 112 and a distal conduit 114b that provides fluid communication between the distal filter element 102 and the inflow opening 112.

Both distal filter element 102 and proximal filer element 108 are integrated structures that substitute for a section of the wall of the filtration catheter, which can have similar diameters to the rest of the catheter. In alternative embodiments, the filter elements can have a slightly different diameter from the remaining portions of the catheter, such as a slightly larger diameter generally without complicating the delivery of the filtration catheter. Also, particular segments of conduits or shaft of the device may or may not have the same diameter as other segments. The filtration catheter has a main lumen 130 that extends from proximal section 110p through the length of the catheter such that the internal lumen of the tubular filter elements, the conduits can all be considered the part of the main lumen. Filtration catheter 100 additionally comprises a proximal balloon 116 and a distal balloon 118 that can extend from the exterior of the shaft. Proximal balloon 116 is positioned between inflow opening 112 and proximal filter element 108 and distal balloon 118 are positioned between inflow opening 112 and distal filter element 102. Other occlusive elements, such as a supported occlusive membrane can be used instead of balloon(s). The balloons and/or the supported membranes used can have appropriate shape, diameter, and composition. Occlusive balloons have been described, for example, in published U.S. patent application 2011/0093000 to Ogle et al., entitled "Vascular Medical Devices With Sealing Elements and Procedures for the Treatment of Isolated Vessel Sections," incorporated herein by reference. In FIG. 1A proximal balloon 116 is shown to have larger diameter than distal balloon 118, which can be appropriate for the respective vessel sizes.

In general, the filter elements can independently have a desired structure with respect to integration of the filter elements into the wall of the catheter. For example, the filters can be formed from a tubular segment with holes drilled through the wall of the tubular segment with diameters selected to block emboli with larger sizes. However, in embodiments of particular interest, the filters are formed from fibers that are formed into tubular sections that replace a section of the catheter wall. As will be discussed further below, the fibers used in the filter elements can be polymer fibers, metal fibers such as Nitinol, or a combination thereof. In some embodiments, filter elements with at least some of the fibers being polymer surface capillary fibers maybe constructed and used. In general, the thickness and shape of the fibers, the tightness or density of the braid or wave of the fibers, the pique per inch of the braid or wave, and the length of the filter elements can all be designed to suit selected filtration performance while balancing the flow through the filters. The length of the proximal filter element and the length of the distal filter element can be the same or different from each other. In the embodiment shown in FIG. 1A, the proximal filter element 108 is longer than distal filter element 102, which can provide greater flow rates into the larger brachiocephalic artery. The diameter of catheter 100 in general can be designed to be suitable for placement inside aortic arch percutaneously. Filter structure 100 may employ radio opaque bands or markers at various location of the catheter body to facilitate visualization during the delivery and placement of the device.

Distal section 110d of the filtration catheter can be designed to restrict or prevent flow of unfiltered blood out from the catheter, and distal section 110d can be designed to facilitate placement of the catheter with the distal section within the left carotid artery. As shown in FIG. 1A, distal section 110d comprises a tapered tip, and filtration catheter 100 can be delivered on a guide wire 120 that extends from a distal guide port 122 at or near the distal end of distal section 110d. In an alternative embodiment shown in FIG. 1H, distal section 121 has an integral wire 123 extending in a distal direction from a closed distal tip. The length of integral wire 123 can be selected to provide for guiding the distal tip along the aortic arch into the left carotid artery and can be, for example, from about 1 cm to about 15 cm, in further embodiments from about 1.5 cm to about 12 cm and in other embodiments from about 2 cm to about 10 cm. A person of ordinary skill in the art will recognize that additional ranges of lengths within the explicit ranges above are contemplates and are within the present disclosure.

In another alternative embodiment shown in FIG. 1I, distal section 131 comprises a separate guide lumen 133 with main lumen 137 within distal section 131 closed to prevent flow of unfiltered blood from distal section 131. Guide lumen 133 is shown with guidewire 135 extending from the distal end of guide lumen 133. Guide lumen 133 can extend along most or all of the length of filter catheter 100 for an over the wire design, or guide lumen 133 can terminate at a location within the patient's vasculature during use for a rapid exchange configuration. In general, with a rapid exchange configuration, guide lumen 133 generally extends in a proximal direction at least past proximal occlusive element. See FIG. 3D below for further discussion of a rapid exchange configuration. With a separate guide lumen, the catheter does not necessarily have a main lumen extending to the proximal end of the catheter.

Cross sectional views along the lines C-C to G-G of the device reveals internal structure of the catheter at various positions along its length. As noted above, in general any reasonable structure can be used for each of the occlusive elements independently selected, such as mechanical occlusive elements, but the discussion herein focuses on balloon based occlusive elements in both positions, which provide convenient functionality for the delivery, deployment and recovery of the catheter. As shown in FIG. 1B, the proximal section 110p of the device can comprises a balloon lumen 124, a balloon lumen 126, and guidewire 120 within main lumen 130. Although the view in FIG. 1B indicates the presence of two balloon lumens that are in fluid communication with the distal and the proximal balloons, the device can also be constructed to have only one balloon lumen in fluid communication with both the distal and the proximal balloons to inflate the balloons. The view in FIG. 1C shows that balloon lumens 124 and 126 and guidewire 120 extend past proximal filter element 108 with fibers 132 surrounding the balloon lumens and the guidewire. The view in FIG. 1D indicates that proximal balloon 116 surrounds bridge section 110b of the catheter and the interior of proximal balloon 116 is in fluid communication with balloon lumen 124 with guidewire 120 extending through proximal conduit 114a. The view in FIG. 1E shows inflow opening 112 on bridge section 110b with only one balloon lumen 126 extending through this part of the catheter and with guidewire 120 extending through conduit 114. The view in FIG. 1F shows that distal balloon 118 surrounds bridge section 110b, and the interior of distal balloon 118 is in fluid communication with balloon lumen 126 with guidewire 120 extending through distal conduit 114b. The view in FIG. 1G shows that guidewire 120 extend past distal filter element 102 with fibers 103 surrounding the guidewire.

As shown in FIG. 1A, in general for over-the-wire embodiments, the proximal end 134 of a proximal section 110p of filtration catheter 100 comprises a proximal port 140 that provides exit of guidewire 120 from the main lumen and other proximal ports such as 138 and 142 that provide inflation or deflation of balloons. Proximal port 140 or other optional ports can provide connection to an aspiration device, such as a syringe or the like, to provide aspiration of the filter elements through the main lumen if desired. Proximal ports 138, 140, 142 can comprise Luer fittings, hemostatic valves or the like.

With respect to the size of the filtration catheter, a larger diameter of the catheter provides a corresponding increase in the ability to allow blood flow into the carotid arteries. The body of the catheter in general can be formed from one or more biocompatible materials, including, for example, metals, such as stainless steel or alloys, e.g., Nitinol, or biocompatible polymers such as polyether-amide block copolymer (PEBAX®), nylon (polyamides), polyolefins, polytetrafluoroethylene, polyesters, polyurethanes, polycarbonates other suitable biocompatible polymers, copolymers thereof or combinations thereof. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. The shaft in general comprises different sections or portions along the length of the device. The different sections or portions of the shaft can be constructed with the same or different materials. In addition, selected sections or portions of the shaft can be formed with materials to introduce desired stiffness/flexibility for the particular section or portion of the catheter. For example, materials with metal wires embedded inside polymer maybe used for polymeric sections of the shaft or in selected sections of the shaft. Upon heating over the softening temperature of the polymer and subsequent cooling, the wire can become embedded within the polymer. Suitable wire includes, for example, stainless steel wire, Nitinol wires or alike, and the wire can be flat or rounded with an appropriate small diameter or thickness. The metal wire can add additional mechanical strength while maintaining appropriate amounts of flexibility for the shaft of the catheter.

In some embodiments, the overall length of the filtration catheter may be approximately 80 cm to 160 cm, in other embodiments, the overall length may be approximately 90 cm to 150 cm, and in additional embodiments, the overall length may be approximately 100 cm to 140 cm. In some embodiment, the filtration catheter can be fit through an introducer sheath, including commercially available sheaths. As a specific example, if a 7 F introducer sheath is used, the outer diameter of the delivered portion of the filtration catheter can have an outer diameter of no more than approximately 0.077 inches. In general, the outer diameter of the filtration catheter may be about 5 Fr (1.67 mm, 0.066 inches) to about 7 Fr (2.3 mm, 0.092 inches), in other embodiments, about 5.5 Fr to about 6.5 Fr, in additional embodiments, from about 5.75 Fr to about 6.25 Fr. A person of ordinary skill in the art will recognize that additional ranges of the filtration catheter length and diameter within the explicit ranges above are contemplated and are within the present disclosure.

The distance between the proximal occlusive element and the distal occlusive element in general need to be long enough for positioning of the proximal occlusive element in the brachiocephalic artery and the distal occlusive element in the carotid artery with a section of the bridging section spanning the aortic arch between the brachiocephalic artery and the left carotid artery. For example, if occlusive balloons are used, the center to center distance between the two balloons or other occlusive elements can be made from about 30 mm to about 120 mm, in other embodiments from about 35 mm to about 110 mm, in further embodiments from about 40 mm to about 100 mm or in some embodiments from about 50 mm to about 90 mm. A person of ordinary skill in the art will recognize that additional ranges of center to center distances within the explicit ranges above are contemplated and are within the present disclosure. Bridge section 110b comprises inflow opening 112 which can be formed through removal of a section of the wall of a tubular element, although the inflow opening can be formed through other structures, such as the physical connection of a proximal tubular element and a distal tubular element with an appropriate connection that provide for flow into the respective tubular elements from the inflow opening at the connection of the elements. Similarly, inflow opening 112 in some embodiments can be essentially an inflow opening in a distal direction and an effectively distinct inflow opening in a proximal direction to respectively provide flow into a distal conduit and a proximal conduit respectively.

FIG. 2A is a fragmentary side view illustrating the proposed blood flow in the filtration catheter 100 when balloons 116, 118 are deployed, i.e., expanded, in positions along the aortic arch. In use, blood potentially with emboli 154 is redirected to enter the inflow opening 112, go through the conduit 114 including 114a, and 114b of the shaft 110 and exit the filtration catheter through the proximal and distal filter elements 108 and 102 respectively as filtered blood 156a and 156b respectively. The arrows in the figure are used to indicate the direction of the blood flow. Also, ancillary components that can be used in conjunction with the filtration catheter are shown. In particular, an obturator 146 as shown in FIG. 2B can be used to facilitate delivery of the filtration catheter, and a sheath 150 with a distal opening 152 as shown in FIG. 2C can be used to facilitate delivery and/or retrieval of the filtration catheter. Obturator 146 can be placed into main lumen 130 to extend through the conduit 114 including the proximal conduit 114a and distal conduit 114b of filtration catheter 100 during delivery over a guidewire 120 through a guide port 148 to protect filter elements 108, 102 from damage during delivery. Obturator 146 can have a guide lumen. Sheath 150 can be positioned over the exterior of filtration catheter 100 to cover at least a portion of the filtration catheter during delivery and/or recovery of the filtration catheter from the patient to protect the filter elements during delivery and/or to further reduce the chance of any emboli escaping from the filter elements during removal. Also, sheath 150 can be used optionally to cover one or both filters and/or the inflow opening in the bridge to facilitate application of suction within the lumen of the filter structure by restricting flow into the main lumen from the inflow opening. Thus, during recovery, sheath optionally can be advanced at least past filter element 102, in some embodiments past the inflow opening 112 and in additional embodiment to cover filter element 108.

FIG. 3A is a schematic diagram illustrating filtration catheter 100 of FIG. 1A placed inside the aortic arch 160 by way of right subclavian artery 162, with proximal portion 136 placed outside the patient. In some embodiment, a guidewire 120 extends through right subclavian artery 162 to aortic arch 160 through brachiocephalic artery 164. Guidewire 120 is extends along aortic arch 160 with a distal portion in left carotid artery 166. With guidewire 120 properly placed inside left carotid artery 166, filtration catheter 100 can then be properly positioned with main catheter lumen 130 over guidewire 120 for use to filter blood flow from the aorta. As shown in FIG. 3A, when properly placed, inflow opening 112 of filtration catheter 100 is located inside aortic arch 160 with bridge section spanning between left carotid artery 166 and brachiocephalic artery 164. Distal balloon 118 and distal filter element 102 are placed inside left carotid artery 166 with distal filter element 102 positioned distally beyond distal balloon 118. Proximal balloon 116 and proximal filter element 108 are placed inside larger brachiocephalic artery 164 with proximal filter element 108 positioned proximally relative to proximal balloon 116.

In the position shown in FIG. 3A, the distal balloon and proximal balloon can be deployed to block unfiltered flow into the carotid arteries. With blood flow redirected by extended balloons, blood from the aorta along the flow indicated with flow arrows 168 enters inflow opening 112 on the shaft of filtration catheter 100, flows through conduit 114 including 114a and 114b and exit the filtration catheter lumen as filtered blood through the distal filter element and proximal filter element to enter into left carotid artery 166 and right carotid artery 170, respectively. The flow of the blood is indicated by flow arrows. As shown in FIG. 3A, deployed filtration catheter 100 occupies a small portion of the space inside the aortic arch 160, leaving the rest of the space for procedures, such as heart valve replacement or other procedures, e.g., endovascular procedures, on or in the vicinity of the heart. Because filter elements 102, 108 of the filtration catheter are an integral part of the filtration catheter, no distinct deployment or collapse of the filter elements associated with other filter designs is involved. After the completion of the operation, the filtration catheter can be simply removed with the emboli trapped inside the conduit or within the braids or waves of the fibers.

As discussed above, the integrated filter element(s) of the filtration catheter can be made of braided fibers at a constant pique. Referring to FIGS. 3B and 3C, photos of a specific embodiment of filter elements 102 and 108 are shown made with fiber braids 104 and 132 forming respective filter element. Emboli 172, 174 are shown to be trapped inside the fiber braids 104 and 132 respectively. The enlarged fiber braids also reveal metal wires or filaments 176 and 178 integrated into the fiber braids of the filter elements of the filtration catheter.

FIG. 3D shows an alternative rapid exchange embodiment of a filtration catheter 200 placed inside the aortic arch 260 by way of the right subclavian artery 262, with a proximal portion 236 positioned outside the patient. Filtration catheter 200 comprises a main or central lumen 230 and a rapid exchange guide wire port 250. Proximal portion 236 may or may not comprise a main lumen if it is desirable to have access to the flow, such as for the delivery of a drug.

Guide wire 220 of the this embodiment can be similarly delivered and positioned inside the aortic arch 260 into the left carotid artery 266 through the brachiocephalic artery 264. With the guidewire 220 successfully delivered and properly placed inside the left carotid artery 266, the filtration catheter 200 can then be delivered over the guidewire 220 that extends through the rapid exchange port 250, with the guide wire 220 exits at the rapid exchange port 250. FIG. 3D shows the inflow opening 212 of the filtration catheter 200 is located inside the aortic arch 260 with the bridge section of the filtration catheter 200 spanning between the left carotid artery 266 and the brachiocephalic artery 264. In general, the rapid exchange catheter embodiments can be designed with the guidewire extending through a main catheter lumen 230 or a distinct guidewire lumen. While shown in FIG. 3D with rapid exchange port 250 positioned in a proximal position relative to proximal filter 208, rapid exchange port 250 can be positioned at any point proximal to proximal occlusive element 216. The distal balloon 218 and the distal filter element 202 are placed inside the left carotid artery 266 with the distal filter element 202 positioned distally beyond the distal balloon 218. The proximal balloon 216 and the proximal filter element 208 are placed inside the larger brachiocephalic artery 264 with the proximal filter element 208 positioned proximally beyond the proximal balloon 216. Arrows 268 are used to indicate blood flow in the aorta enters the inflow opening 212 of the filtration catheter 200, travel through the conduit 214 including 214a, and 214b and exit as filtered blood through the distal filter element and proximal filter element to enter into the left carotid artery 266 and the right carotid artery 270, respectively.

Second Type of Filtration System

Referring to FIG. 4A, a filtration system 300 is illustrated to exemplify the features of the second type of filtration system. FIG. 4A is a fragmentary side view of the filtration catheter 304 with a proximal portion 336 and a filter device 350 integrated with the filtration catheter 304 to represent an embodiment of the second type of filtration system 300. Enlarged cross sectional views along the B-B, C-C, and D-D lines of the filtration system 300 are illustrated in FIGS. 4B-4D respectively. The filtration catheter 304 can be used with other embolic protection filter device, such as commercially available FIBERNET®, SPIDER™, and FILTERWIRE™. The filter device in general comprises a filter element that is supported on a guide structure. Because this filter element is independent from the filtration catheter, it is generally referred to as the independent filter element to differentiate from the integrated filter elements of the filtration catheters discussed herein. As shown in FIG. 4A, filter device 350 extends through the lumen 330 of filtration catheter 304. As illustrated in this embodiment, filter device 350 comprises a basket type filter element 352 associated with the guide structure 320. An enlarged view of basket type filter element 352 is shown in FIG. 4E. Features of the filter element 352 can be seen in this detailed view. Specifically, the independent filter element 352 comprises a filter basket 354 that is integrated with an optional strut 356 that is associated with the guide structure 320. When pushed by a retrieval catheter, strut 356 can facilitate collapse of filter basket 354 into a low profile retrieval configuration. Filter device 350 may optionally comprise a distal tip 358 that extends distally beyond the filter basket, which may or may not be an extension of guide structure 320.

Referring to FIG. 4A, the filtration catheter 304 comprises a shaft 306, an integrated filter element 308, a distal section 310d extending in a distal orientation from the integrated filter element 308, a balloon 316 associated with the exterior of the distal section at or near the distal end of the catheter, a distal opening 312, and a conduit 314, which is a lumen within distal section 310d, that provides fluid communication between the integrated filter element 308 and the distal opening 312. A proximal portion 336 is connected at or near the proximal end of shaft 306. The integrated filter element 308 allows fluid to flow through the wall of the catheter and being filtered. The length of filtration catheter can be from about 60 cm to about 180 cm, in further embodiments from about 70 cm to about 160 cm and in other embodiments from about 80 cm to about 150 cm. A person of ordinary skill in the art will recognize that additional ranges within the explicit ranges are contemplated and are within the present disclosure. The integrated filer element 308 is a fully integrated structure that is a part of filtration catheter 304, which can have similar diameters to the rest of the catheter, or more particularly to adjacent sections of the catheter at the distal side and the proximal side of the integrated filter element. In alternative embodiments, the filter element can have a slightly different outer diameter from the adjacent portions of the catheter, such as a slightly larger outer diameter generally without complicating the delivery of the filtration catheter. Also, particular segments of the catheter may or may not have the same diameter or material as other segments. For example, the distal section 310d of the catheter may comprise a distal tip 322 that is made of different material from the rest of the catheter shaft, and distal section 310d can have a different outer diameter relative to shaft 306. In general, the inner diameter of an integrated filter structure is roughly equal to or greater than the inner diameters of the adjacent sections of catheter, although the inner diameter of the integrated filter may be smaller than the inner diameter of adjacent sections if this structure does not interfere with other structures or functions. In embodiments with a rapid exchange configuration, the rapid exchange port for passage of a guide structure associated with the independent filter element can be placed between the integrated filter and the occlusive device so that the guide structure does not pass through the lumen of the integrated filter.

In over-the-wire embodiments, the filtration catheter 304 can have a main lumen 330 that extends through the length of the catheter such that the internal lumen 318 of the integrated filter element and the conduit 314 can all be considered part of the main lumen. The balloon 316 is positioned between the distal opening 312 and the integrated filter element 308. Other occlusive elements, such as a supported occlusive membrane can be used instead of balloon(s). The balloons and/or the supported membranes used can have appropriate shape, diameter, and composition. Occlusive balloons have been described, for example, in published U.S. patent application 2011/0093000 to Ogle et al., entitled "Vascular Medical Devices with Sealing Elements and Procedures for the Treatment of Isolated Vessel Sections," incorporated herein by reference. In FIG. 4A the balloon 316 is shown in an extended configuration, the extended diameter of the balloon is appropriate for occlusion of specific vessel size. For rapid exchange embodiments, the filtration catheter may or may not have a main lumen. For appropriate embodiments, a balloon lumen extends from proximal end 334 to balloon 316.

In general, the integrated filter element can have a desired structure with respect to integration of the filter element into the wall of the catheter. For example, the filter element can be formed from a sheet with holes drilled through the sheet with diameters selected to block emboli with larger sizes. However, in embodiments of particular interest, the filter element is formed from fibers that are braided, woven or otherwise formed into tubular section that can be used to replace a section of the catheter wall. The fibers used in the filter element can be polymer fibers, metal fibers such as Nitinol, or a combination thereof. In some embodiments, filter element with at least some of the fibers being polymer surface capillary fibers maybe constructed and used. In general, the thickness and shape of the fibers, the tightness or density of the braid or wave of the fibers, the pique per inch of the braid or wave, and the length of the filter element can all be designed to suit selected filtration performance while balancing the flow through the filters. Longer filter elements in general can provide greater flow rate compared to filter element that is relatively shorter. The filtration catheter 304 may employ radio opaque bands or markers at various locations of the catheter body to facilitate visualization during the delivery and placement of the catheter.

Cross sectional views along the lines B-B to D-D of the filtration system 300 reveals internal structure of the catheter shaft at various positions along its length for this embodiment. As noted above, in general any reasonable structure can be used for the occlusive element, such as mechanical occlusive element, but the discussion herein focuses on balloon based occlusive element, which provides convenient functionality for the delivery, deployment and recovery of the catheter. As shown in FIG. 4B, the shaft of the catheter can comprise a balloon lumen 324, and a guide structure 320 within a main lumen 330. The view in FIG. 4C shows the internal lumen 318 of the integrated filter element with the balloon lumen 324 and the guide structure 320 extending past the filter element 308 with fibers 332 surrounding the balloon lumen 324 and the guide structure 320. The view in FIG. 4D indicates that the balloon 316 surrounds the conduit 314 of the filtration catheter and the interior of the balloon 316 is in fluid communication with the balloon lumen 324. The guide structure 320 is shown to extend through the conduit 314 of the catheter in FIG. 4D.

The proximal portion 336 of the filtration catheter 304 is shown to comprise a proximal port 340 that provides exit for guide structure 320 from the main lumen, a proximal port such as 338 that provides inflation or deflation of balloon 316, and an optional additional proximal port 342 that can an provide connection to an aspiration device, such as a syringe or the like, to provide aspiration of the filter element through the main lumen if desired. Proximal ports 338, 340, 342 can comprise Luer fittings, hemostatic valves and/or the like.

With respect to the size of the second type of filtration catheter, a larger diameter of the catheter, at least with respect to its distal portion, provides a corresponding increase in the ability to allow blood flow into the carotid arteries. The body of the catheter in general can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, other suitable biocompatible polymers, copolymers thereof or combinations thereof. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. The shaft in general comprises different sections or portions along the length of the device. The different sections or portions of the shaft can be constructed with the same or different materials. In addition, selected sections or portions of the shaft can be formed with materials to introduce desired stiffness/flexibility for the particular section or portion of the catheter. For example, materials with metal wires embedded inside polymer maybe used for polymeric sections of the shaft or in selected sections of the shaft. Upon heating over the softening temperature of the polymer and subsequent cooling, the wire can become embedded within the polymer. Suitable wire includes, for example, stainless steel wire, Nitinol wires or alike, and the wire can be flat or rounded with an appropriate small diameter or thickness. The metal wire can add additional mechanical strength while maintaining appropriate amounts of flexibility for the shaft of the catheter.

In some embodiments, the overall length of the second type of filtration catheter may be approximately 40 cm to 200 cm, in other embodiments, the overall length may be approximately 50 cm to 180 cm, and in additional embodiments, the overall length may be approximately 60 cm to 160 cm. In some embodiment, the filtration catheter can be fit through an introducer sheath, including commercially available sheaths. As a specific example, if a 7 F introducer sheath is used, the outer diameter of the delivered portion of the filtration catheter can have an outer diameter of no more than approximately 0.077 inches. In general, the outer diameter of the filtration catheter may be about 5 Fr to about 7 Fr, in other embodiments, about 5.5 Fr to about 6.5 Fr, in additional embodiments, about 6 Fr. A person of ordinary skill in the art will recognize that additional ranges of the filtration catheter length and diameter within the explicit ranges above are contemplated and are within the present disclosure.

Figure 5A:
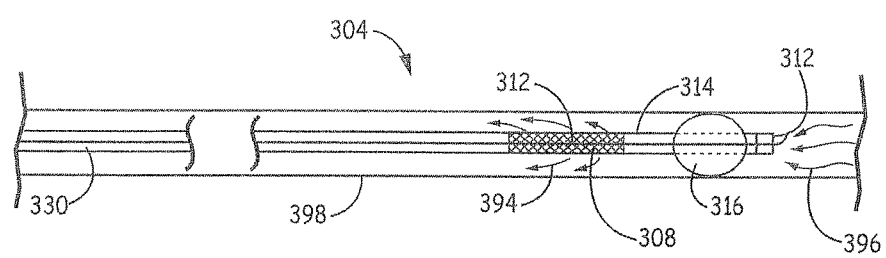
FIG. 5A is a schematic diagram of the filtration catheter of FIG. 4A placed inside a blood vessel with arrows illustrating blood flow through the conduit and the integrated filter element.
Figure 5B:
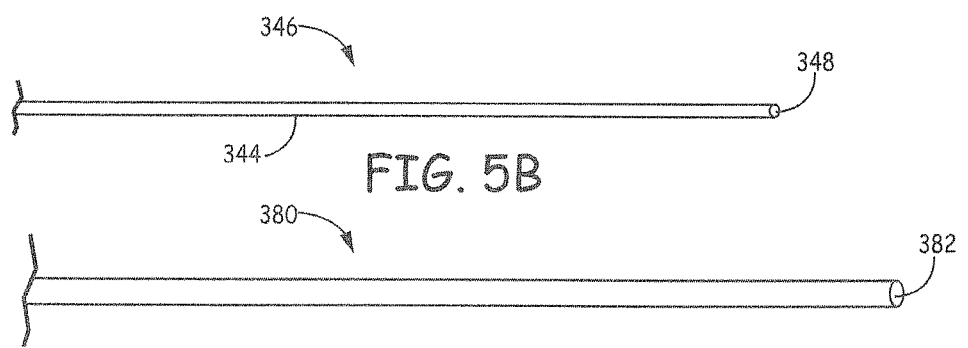
FIG. 5B is a side view of an obturator that can be used to facilitate delivery of the filtration catheter of FIG. 4A.
Figure 5C:
FIG. 5C is a side view of a sheath that can be used to facilitate retrieval of the filtration system of FIG. 4A.

A fragmentary side view illustrating proposed blood flow in a vessel 398 when the filter catheter 304 is deployed is shown in FIG. 5A. Specifically, balloon 316 is deployed to contact the wall of the vessel 398. Blood flow 396 in the vessel enters the distal opening 312, goes through conduit 314 and exits the filtration catheter 304 through the integrated filter element 308 as filtered blood 394. The arrows in the figures are used to indicate the direction of the blood flow. Ancillary components that can be used in conjunction with the filtration catheter are shown in FIG. 5B and FIG. 5C. Specifically, an obturator 346 as shown in FIG. 5B can be used to facilitate delivery of the filtration catheter, and a sheath 380 with a distal opening 382 as shown in FIG. 5C can be used to facilitate delivery and/or retrieval of the filtration catheter. The obturator 346 would be placed into the main lumen 330 of the filtration catheter including internal lumen 318 of the integrated filter element 308 and the conduit 314 during delivery over a guide structure through a guide port 348 to protect the integrated filter element 308 from damage during delivery. Obturator 346 can have a guide lumen 344. Sheath 380 can be positioned over the exterior of the filtration catheter 304 to cover at least a portion of the filtration catheter during delivery and/or recovery of the filtration catheter from the patient to protect the filter element 308 during delivery and/or to further reduce the chance of any emboli escaping from the filter elements during removal and to optionally provide for the successful application of suction within the lumen of the filter structure by restricting flow into the main lumen 330 from the distal opening 312. Thus, during recovery, the sheath 380 can be advanced to cover filter element 308. A catheter or sheath can also be used to facilitate retrieval of the independent filter element of the second type of filtration system. For example, in some embodiments a catheter can be delivered through the lumen of the second filtration catheter along the guide structure of the independent filter element to collapse a basket type filter element into a retrieval configuration or generally cover the filter element if already in a retrieval configuration through the manipulation of the guide structure alone. In further embodiments, a catheter can be used to provide aspiration during the retrieval of an independent filter, such as a FIBERNET® filter.

Occlusive Elements

The occlusive elements of either type of filtration catheters are designed to stop direct blood and emboli flow into the carotid arteries and redirect the flow through an integrated filter element of the catheters. The occlusive elements generally have an un-extended delivery configuration and an extended deployed configuration. In the extended deployed configuration, the occlusive element has the appropriate diameter and mechanical flexibility to form contact with surrounding blood vessel to reduce or eliminate passage of blood. The balloons used as the occlusive elements in the catheters can generally be inflated using saline or other appropriate fluid. In embodiments where a supported membrane is used as occlusive elements, a spring metal frame can be used as the supporting means, which can resume an extended configuration upon release, and various other mechanical occlusive elements can be used with an extended deployed configuration, if desired. Balloons, membranes, and the like can be formed from suitable polymers including elastic polymers and the like. Suitable polymers include polyether-amide block co-polymer (PEBAX®), nylon (polyamides), polyolefins, polytetrafluoroethylene, polyesters, polyurethanes, polycarbonates or other suitable biocompatible polymers. For compliant balloons, suitable elastic polymers, such as thermoplastic elastomers, can be used to form the balloon include, for example, Pebax® (poly (ether-block-amide)), low durometer polyurethanes, styrene-butadiene copolymers, latex, polyisoprene, synthetic rubbers and the like.

In some embodiments, a compliant balloon can have a length along the catheter from about 2 mm to about 25 mm, in other embodiments from about 3 mm to about 20 mm and in additional embodiments from about 4 mm to about 18 mm. In general, for the first type of filtration system, because the distal balloon or occlusive element is deployed in the left carotid while the proximal balloon or occlusive element is deployed in the brachiocephalic artery, the proximal balloon generally has a bigger diameter when inflated. For example, in some embodiments, the inflated proximal balloon or other extended proximal occlusive element can have an outer diameter from about 6 mm to about 25 mm, in some embodiments from about 8 mm to about 22 mm and in further embodiments from about 9 mm to about 20 mm. Similarly, the inflated distal balloon or other extended distal occlusive device can have an outer diameter from about 4 mm to about 16 mm, in some embodiments from about 5 mm to about 15 mm and in further embodiments from about 6 mm to about 16 mm. The diameter of the occlusive element for the second type of filtration catheter can be made comparable to the proximal occlusive element of the first type of filtration catheter for deployment in the brachiocephalic artery. Other sizes for the occlusive element can be adopted for other type of blood vessel sizes accordingly. A person of ordinary skill in the art will recognize that additional ranges of lengths and diameters within the explicit ranges above are contemplated and are within the present disclosure.

Filter Elements

The filter elements for either type of filtration systems are designed to allow blood to flow to the right and left carotid arteries while entrap clinically significant emboli. The diameter of the integrated filter element for example can be similar to the diameter of the remaining shaft of the catheter. The length of the integrated filter element along the axis of the catheter can be selected to be large enough to achieve a desired flow rate through the filter. However, constraints in the vessel can limit the length of the filter, and filter design to achieve appropriate levels of mechanical strength can become more complicated for longer filters. For example, due to greater flow desired through the proximal filter of the first type of filter catheter, the proximal filter can generally have a greater length than the distal filter as well as potentially a greater diameter. In general, the proximal filter can have a length from about 10 mm to about 100 mm, in some embodiments from about 20 mm to about 80 mm and in further embodiments from about 25 mm to about 75 mm. The distal filter can have a length from about 5 mm to about 30 mm and in further embodiments from about 6 mm to about 20 mm. The length of the integrated filter element for the second type of filtration catheter can be made comparable to the proximal filter element of the first type of filtration catheter. Other lengths of the integrated filter element can be adopted for other type of blood vessel sizes accordingly. A person of ordinary skill in the art will recognize that additional ranges of filter lengths within the explicit ranges above are contemplated and are within the present disclosure.

While the filter can comprise a solid membrane with drilled holes or the like, the integrated filter elements in general can be formed effectively from fibers, filaments, wires, and/or yarns that are weaved, braided, and/or knitted to form an approximately tubular filter element. The filter element can comprise, for example, bundles of fibers, fiber yarns, metallic wires or a combination thereof, braided at a constant or variable pique per inch. The filter element in general is incorporated into the catheter structure to replace a portion of the catheter shaft so fluid from the interior of the catheter can exit the catheter through the filter elements while emboli is trapped or retained by the integrated filter element. In some embodiments, the filter elements can be designed to capture most emboli, i.e. at least about 95%, with an average diameter of at least about 50 micron. In some embodiments, the filter elements may have effective pore sizes of about 30 micron to about 600 micron, in other embodiments, about 40 micron to about 500 micron, in additional embodiments about 50 micron to about 250 micron. A person of ordinary skill in the art will recognize that additional ranges of pore sizes within the explicit ranges above are contemplated and are within the present disclosure.

In general, the fibers used in the filter elements can have circular cross sections or non-circular cross sections, such as an oval cross section. In some embodiments, suitable fibers can have diameters from 5 microns to about 150 microns, in further embodiments from about 7.5 microns to about 125 microns, and in additional embodiments from about 10 microns to about 100 microns. A person of ordinary skill in the art will recognize that additional ranges of diameters within the explicit ranges above are contemplated and are within the present disclosure. In some embodiments, the fibers used in the filter elements comprise surface capillary (SCF) fibers. For example, the SCF fibers can be used together with other type of fibers and/or elements to provide filter elements with desired filtration property and mechanical strength. The use of SCF fibers can be particularly desirable for the independent filter element of the second type of filtration system as discussed further below along with a more detailed discussion about properties of SCF fibers in general. The number and thickness of metal wires can be selected to provide a desired degree of mechanical integrity to the filter structure, and polymer fibers can be woven appropriately to take advantage of the structural stability provided by the metal wires. The number of polymer fibers and the weave can be similarly selected to provide a desired degree of filtration and flow through the filter. For example, in some embodiments, 5-50 strands of stainless steel or titanium wire with a diameter from about 0.0005 inch to about 0.005 inch can be used to provide support in a selected weave. As an example of the polymer strands, 10-100 strands with 5-50 filaments per stand of 100 denier to 100 denier filaments can be woven into the filter element around the metal wire support. Various ways can be incorporated into to the weave to integrate the metal wires and polymer fibers based on known weaving approaches in the art.

The selection of the composition for the fibers including the SCF fibers can provide further flexibility to the properties of the fiber for a particular filter element design. For example for polymeric fibers, the fiber polymer composition can modulate the hydrophobic or hydrophilic nature of the filter elements, or the polymer may elute controlled released drugs. Furthermore, the fibers can incorporate coatings or the like that can further modify the fiber properties. Additionally, metal wires, such as stainless steel or alloys, e.g., Nitinol, can be used in place of or in conjunction with the polymeric fibers to provide physical integrity, strength and flexibility of the filter element. Referring to FIGS. 3B and 3C, for example, the integrated filter element comprises metal wires 176 to provide mechanical strength to the filter element. In general the metal wires can be round, flat, oval or other shape. The polymer used herein generally can incorporate certain desired properties of medical polymers, such as established biostability, strength, and flexibility. In some embodiments, the fibers are formed from polymers, such as commercially available polyester (PET) fibers, polyetherimide fibers such as Ultem, and/or aramid fibers such as Kevlar or Nomex. In some embodiment fibers with relatively higher temperature resistance can be used so the fiber elements can be better integrated into the shaft of the device. Suitable polymers include, for example, polyamides (e.g., nylon), polyesters (e.g., polyethylene teraphthalate), polyacetals/polyketals, polyimide, polystyrenes, polyacrylates, polylactic acid, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. In some embodiments, radiopaque fibers including metal wires can be used in the filter element. For example the use of radiopaque polymer fibers in filter elements is discussed in the published U.S. patent application 2007/0172526A to Galdonik et al., entitled "Radiopaque Fibers and Filtration Matrices," incorporated herein by reference.

Surface Capillary Fibers

Surface capillary fibers (SCFs) are known to provide desirable filtration properties in embolic protection devices for use in arteries. The formation of vascular filters with an unwoven mat of SCF fibers for example is described in U.S. Pat. No. 7,879,062 to Galdonik et al., entitled "Fiber Based Embolism Protection Device," incorporated herein by reference. Embolism protection devices formed with surface capillary fibers in commercial embodiments such as FiberNet® from Medtronic, Inc. provide excellent filtering properties and are discussed in more detail below.

A schematic cross section of an embodiment of a surface capillary fiber 480 is shown in FIG. 5D, along with a cross section of two contrasting round fibers 482 and 484 shown in FIGS. 5E and 5F respectively. SCF fibers are characterized by surface channels or capillaries 486 formed along the surface of the fiber. Surface capillaries are characterized by having a portion of the capillary exposed at the surface of the fiber along the length of the fiber. The surface capillaries result in significant increase in the surface area of the fibers relative to fibers with a smooth surface and the same diameter. The surface capillaries generally run along the length of the fiber. An SCF fiber can have surface channels that essentially make up a large fraction of the bulk of the fiber such that little if any of the interior mass of the fiber is not associated with walls of one or more surface capillaries. The surface channels of the SCF can impart excellent fluid transfer properties. In addition, the surface channels can house a therapeutic agent if desired. These fibers can help facilitate excellent flow maintenance (even after embolic entrapment) and entrapment of very small particles (~40 microns). The SCF fiber substrate can be formed with a relatively complex cross-sectional geometry. Generally, the SCF fibers are formed from polymers, such as organic polymers, which can be formed into SCF fibers by extrusion. Suitable approaches for the manufacture of the SCF are described in, for example, U.S. Pat. No. 5,200,248 to Thompson et al., entitled "Open Capillary Structures, Improved Process For Making Channel Structures And Extrusion Die For Use Therein," incorporated herein by reference. Geometries of the cross section of the SCF can be selected to be particularly advantageous for a particular application. Suitable fiber geometries include, for example, 4DG™ fibers ranging from about 1 denier to about 1000 denier in size (Fiber Innovation Technology, Inc., Johnson City, Tenn.) but would also include other fiber geometries.

FIBERNET type of filters has been shown to be particularly effective in carotid artery embolic protection as discussed in the U.S. Pat. No. 7,879,062 cited above. An embodiment of the FIBERNET type of filter device 400 is illustrated in FIG. 5G. The filter device 400 can comprise a guide structure 402 that comprises an overtube 406, a corewire 408 with a proximal end 410, and a filter element 420. An actuation tool for the filter is described further in U.S. Pat. No. 8,070,694 to Galdonik et al., entitled "Fiber Based Medical Devices and Aspiration Catheters," incorporated herein by reference. The overtube 406 can have a tapered section 412 with a wire coil 414 adjacent tapered section 412. Corewire 408 can be covered with a coil 416 at its distal end. In this embodiment, the filter element 420 generally comprises a bundle of SCF fibers 404 that is shown in a flared up configuration. The flared fibers 404 is believed to form a porous three dimensional filtration matrix that comprises a plurality of effective pores that are sized to trap emboli. The filter device can be used in conjunction with the second type of filtration catheter to form embodiments of second type of filtration system that are particularly suitable for embolic protection during heart surgeries. An embodiment of the second type of filtration system combining the filtration catheter 304 of FIG. 4A with the FIBER- NET type of filter device 400 illustrated in FIG. 5G is shown and discussed below in FIG. 8B.

Specific Filtration Catheter Design

A specific design of the first type of filtration catheter with distal ports and various cross sections of the shaft are illustrated in FIGS. 6, 6A-6G. Specifically, FIG. 6 is a fragmentary side view of a filtration catheter 500 according to one embodiment of the first type of filtration system. Enlarged cross sectional views of the catheter 500 along the A-A, B-B, C-C, D-D, and E-E lines are illustrated in FIGS. 6A-6E respectively. As shown in FIG. 6, the filtration catheter 500 comprises a distal filter element 502, a proximal filter element 508, an inflow opening 512 on the shaft between the two filter elements, a main lumen 530, and a distal port 522. Both the distal filter element 502 and the proximal filer element 508 are a part of the catheter that is integrated with the rest of catheter body. The proximal filter element 508 can be longer than the distal filter element 502 to accommodate the larger blood flow into the brachiocephalic artery. For example, in this device the distal filter element 502 is about 20 mm in length while the proximal filter element 508 is about 30 mm in length. The filtration catheter 500 additionally comprises a proximal balloon 516 and a distal balloon 518 that can extend from the exterior of the catheter. The proximal balloon 516 is positioned between the inflow opening 512 and the proximal filter element 508, and the distal balloon 518 is positioned between the inflow opening 512 and the distal filter element 502. The distance between the proximal balloon 516 and the distal balloon 518 in general need to be long enough to span between and to access the entrances of the brachiocephalic artery and the left carotid artery. The filtration catheter 500 additionally employs radio opaque bands 506 to facilitate visualization during the delivery and placement of the device, and the number of radiopaque marker bands and their location can be selected as desired to facilitate the procedure.

Cross sectional views along the lines A-A to E-E of the filtration catheter reveal internal structure of the catheter shaft. As shown in FIGS. 6A and 6B, the filtration catheter 500 comprises a main lumen 530 that houses a balloon lumen 524 and a balloon lumen 526 that are parallel to each other. The view in FIG. 6C indicates that the catheter comprises only one balloon lumen 526 and with the other balloon lumen 524 terminated after connection with the interior of proximal balloon 516. The view in FIG. 6D shows the inflow opening 512 on the catheter with only one balloon lumen 526 extending through this part of the shaft. This part of main lumen 530 can also be referred to as conduit. The view in FIG. 6E indicates the tapered tip portion of the filtration catheter with a distal guide port 522. The filtration catheter 500 illustrated does not have a separate guidewire lumen. In addition to providing fluid communication between different parts of the catheter, The main lumen 530 also serves as a guidewire lumen. The filtration catheter therefore can be tracked directly through the distal guide port 522 on a guidewire. FIG. 6F shows fitting or connector 550 with the proximal ports 538, 540, and 542 that can be connected to the filtration catheter 500 via a connector 544. In terms of usage, proximal port 540 for example can provide exit for a guidewire or alike and proximal ports 538 and 542 can provide inflation or deflation of balloons and optional connection to an aspiration device, such as a syringe or the like, to provide aspiration of the filter element(s) through the main lumen if desired. FIG. 6G is a plan view of connector 550 of FIG. 6F looking in a proximal direction along the longitudinal axis with all three ports 538, 540, and 542 aligned in the same plain as that of connector 544.

Use of Filtration Systems for Embolic Protection

The filtration systems described herein can be effectively used for embolic protection of carotid arteries during and/or following procedures on the heart. In particular, the filtration systems described herein can be used to provide embolic protection during endovascular cardiac procedures, such as procedures performed in or around the left atrium and left ventricle of the heart, although the filtration systems may also be useful for procedures on the heart with an approach through the patient's chest. Some procedures may involve an endovascular approach to the heart to accomplish certain steps of the procedure and less invasive approaches through the patient's chest for other aspects of the procedure, such as providing cardiopulmonary bypass. The procedures on the heart can result in emboli that can flow from the aorta and then for circulation to other parts of the body. While emboli can be undesirable in any vessel, the circulation of emboli into the carotid arteries, and in particular the internal carotid arteries, can result in the flow to the patient's brain where the emboli can cause strokes or other adverse consequences. Therefore, it is very desirable to filter emboli from the flow into the internal carotid arteries. Thus, in some embodiments, filter elements associated with the filtration systems described herein can be placed so that emboli are removed from flow into the carotid arteries without removing emboli from flow through the descending aorta and/or one or both of the subclavian arteries where emboli generally may not present a significant concern. When the risk for emboli formation is reduced or eliminated, filtrations systems along with the filter elements may be safely withdrawn from the patient.

Emboli can be released into the blood flow from various procedures on the heart. In particular, heart valve replacement involves significant manipulations of the heart tissue and can be associated with a risk of emboli generation. Other heart procedures include, for example, heart valve repair procedures. Emboli that are generated within or near the left heart chambers may be released into the aorta upon resumption of heart pumping if cardiopulmonary bypass is used. Emboli released into the ascending aorta can flow downstream and may generate a risk of emboli within the carotid arteries. In some embodiments, heart procedures of interest include, for example, endovascular procedures in which instruments are delivered in a percutaneous format up an artery, such as the femoral artery or a subclavian artery to reach the heart.

While the filtering procedures described herein are applicable for protection during various heart procedures, the procedures can be advantageously used in conjunction with performing percutaneous heart valve replacement. Generally, a percutaneous procedure to replace the aortic valve comprises delivery of a prosthetic heart valve through a patient's peripheral vasculature to an area at or near the valve root, such as the aortic annulus or the mitral valve annulus. The valve replacement procedure may comprise the excising of the native valve, although in some embodiments, the replacement valve can be placed within the native valve without removing the native valve. The patient may be placed on cardiopulmonary bypass to provide for oxygenated blood flow while the valve is being replaced. The prosthetic heart valve can be delivered as a single unit or it can be delivered as a plurality of sub-units and assembled in the patient's body. The procedure further comprises implantation of the prosthesis in the desired location. Where the prosthesis comprises a plurality of sub-units, the components of the prosthetic valve can be assembled prior to implantation and/or assembled within the patient.

In some embodiments, a method for performing such a percutaneous valve replacement procedure comprises the delivery of a compressible prosthetic aortic valve comprising a tissue engaging base, designed to hold the prosthesis in place at or near the annulus of the native valve, and a leaflet element, designed to function as a valve. The prosthesis can comprise a plastically deformable structure that is designed to retain its configuration when crimped for delivery. The prosthesis can be affixed to a delivery catheter comprising, concentrically, an outer sheath, an optional push catheter, and a balloon catheter, and the prosthesis can be attached to the balloon catheter such that when the balloon is inflated, the prosthesis adopts its expanded configuration. The catheter can be tracked into the region of the valve annulus from a variety of peripheral arteries or veins, for example, the left femoral artery or right femoral artery. The outer sheath can be tracked into the ascending aorta from a peripheral artery, for example, using a variety of standard techniques such as with the use of a guidewire. When the prosthesis reaches the desired location within the aortic annulus, the outer sheath is pulled back, exposing the prosthetic valve element. In appropriate embodiments, the balloon is then expanded, placing the prosthesis in its expanded configuration. The balloon is then deflated and the delivery structure removed. For alternative embodiments in which the prosthesis has a self-expanding design, simply removing the prosthesis from the outer sheath can induce an expanded configuration. Further discussion on this heart valve replacement procedure as well as alternative embodiments can be found in U.S. Pat. No. 6,454,799 to Schreck, entitled "Minimally-Invasive Heart Valves and Methods of Use," incorporated herein by reference. Heart valve prostheses that can be placed in an aortic valve position or mitral valve positions with or without removing the native valve are described further in U.S. Pat. No. 7,329,278 to Seguin et al., entitled "Prosthetic Valve for Transluminal Delivery," incorporated herein by reference.

The filtration systems described herein can be used to provide embolic protection for selected vessels during a particular heart procedure. The filtration system is generally guided into position through a selected artery, e.g., brachial artery or radial artery in the arm leading to the brachiocephalic artery. The various filtration system designs described above are generally designed for delivery through a right subclavian artery to access the brachiocephalic artery. In general, the filtration system described herein is designed appropriately following deployment to avoid interfering with any tools used to perform the heart procedure. Specifically, the deployment of the first type of filtration system involves deployment of the occlusive elements so the blood flow can be redirected and filtered. The deployment of the second type of filtration system involves both the deployment of the occlusive element as well as the delivery of the filter device and deployment of the independent filter element of the filter device.

In general, the filtration system can be deployed at a selected time, which generally is prior to the time at which there is a significant risk for emboli generation. The appropriate timing for deployment of the filtration system generally depends significantly on the nature of the heart procedure. In some embodiments, if the filtration system does not interfere with any of the heart procedure steps or instruments, the filtration system can be deployed prior to any significant portions of the heart procedure. If good flow is maintained across the filter elements during the whole procedure, the filtration system can be left in place for a significant period of time without any adverse effects. In some embodiments, some steps of the heart procedure may be performed prior to the placement of the filtration system. It may be advantageous to deliver and deploy the filtration system at a later stage if the early steps of the heart procedure do not generate a significant embolic risk and/or if the early steps of the heart procedure could determine that the continuation of the heart procedure is contraindicated. The filtration system though is generally delivered and deployed prior to any significant risk of emboli generation within the aorta.

After the significant risk for emboli generation has passed, the filtration system can be removed from the patient. In some embodiments, the filtration system can be removed after the heart procedure has completed. It may be desirable to continue filtration until after cardiopulmonary bypass has been ended and the natural heart function has been restored for a period of time. If some steps of heart procedure do not generate a significant risk from emboli or if the filtration system may interfere with some steps of the heart procedure, the filtration system may be removed prior to completing all of the steps of the heart procedure. Furthermore, the filtration system can be removed at one stage in the procedure and replaced with another filtration system at a later stage of the procedure.

Generally, to effectuate the removal of the first type of filtration catheter from the patient, the occlusive elements of the catheter can be collapsed to a recovery configuration and the filtration catheter removed from the vessel. The steps to accomplish these objectives depend significantly on the design of the occlusive elements and/or the filter device. For example, the occlusive elements may be collapsed with a sheath or the like to mechanically collapse the occlusive elements. Balloons can be placed in a recovery configuration by deflating the balloons.

The removal of the second type of filtration system involves the removal of the filter device along with the removal of the filtration catheter. In general, the order of removal of the filtration catheter and the independent filter element can be performed for convenience as well as to reduce the chance of releasing any emboli. For example, the filtration catheter can be removed first to make it easier to introduce a separate catheter to facilitate removal of the independent filter element. On the other hand, if the filtration catheter, optionally covered with a sheath or the like, is used to facilitate removal of the independent filter catheter, the two components can be removed together. Thus, various procedures can be used for safe removal of the second type of filtration system from the patient.

Regardless of the design of the occlusive elements, a sheath can be used to facilitate recovery of the filter catheter to cover one or both filters and/or to cover the inflow opening for the first type of filtration system. Catheter or sheath may be used to facilitate the collapsing or simply covering of the independent filter element in the second type of filtration system. In some embodiments, suction may be applied during some portion of the process to facilitate the removal of the filtration system from the vessel. If suction is applied during the retrieval of the first type of filtration system, the inflow opening maybe covered with a sheath so suction can be transmitted effectively to both filter elements. If suction is applied during the retrieval of the independent filter element of the second type of filtration system, a sheath maybe used to cover the filter element to avoid release of the captured emboli. The use of suction for the recovery of a filter device has been discussed for example in published U.S. Pat. No. 8,021,351 to Boldenow et al., entitled "Tracking Aspiration Catheter," and published U.S. patent application 2005/0277976 to Galdonik et al., entitled "Emboli Filter Export System," both of which are incorporated herein by reference.

The procedures described herein generally involve access to the patient's vascular system through a small hole. Generally, the selected vessel can be accessed, for example, with conventional tools, such as introducers, cannula and the like. Hemostatic valves, Luer fittings, other fittings and the like can be used to reduce bleeding from the patient during the procedure. The fittings provide for the introduction and removal of various devices at appropriate times in the procedure.

Figure 7A:
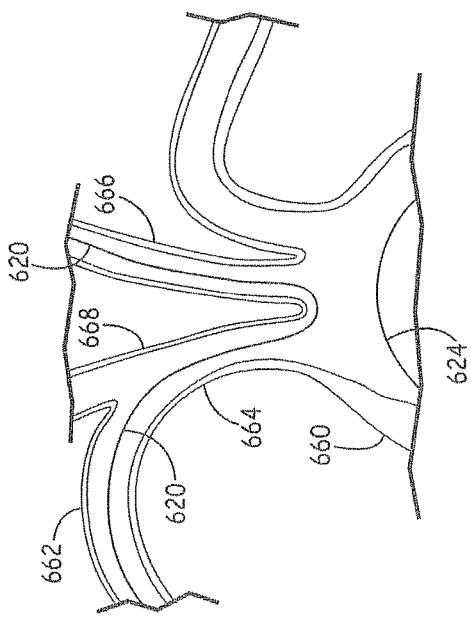
FIGS. 7A-7L are a set of drawings illustrating steps of a representative process of using a filtration catheter during an endovascular procedure.
Figure 7B:
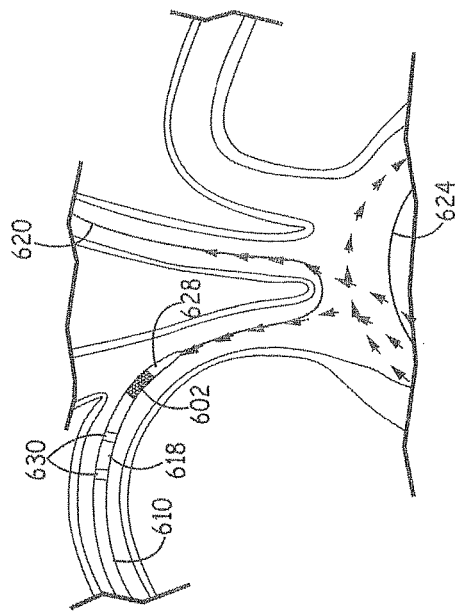

FIGS. 7A-7L illustrates an example of a process of using a first type of filtration catheter 610 during an endovascular procedure. Referring to FIG. 7A, a guide wire 620 can be delivered from the right subclavian artery 662, past the entrance of the right carotid artery 668, along an aortic arch 660 through the brachiocephalic artery 664, and into the left carotid artery 666. A separate guide structure 624 can be delivered into the aortic arch to facilitate performance of a procedure on the heart. As shown in FIG. 7A, there is no interference between the guide structure 624 and the guide wire 620. Referring to FIG. 7B, filtration catheter 610 with a tapered distal tip 628 is delivered along the guidewire 620 while separate guide structure 624 is deployed in the aorta to facilitate a procedure on or near the heart. A distal filter element 602 is integrated into the shaft and connected proximally to the tapered tip 628. Distal balloon 618 is shown in a low profile delivery configuration with two radio opaque marker bands 630 indicating the boundaries of the balloon. Natural blood flow from aorta to the surrounding vessels is indicated by the small arrows in FIG. 7B.

Figure 7C:
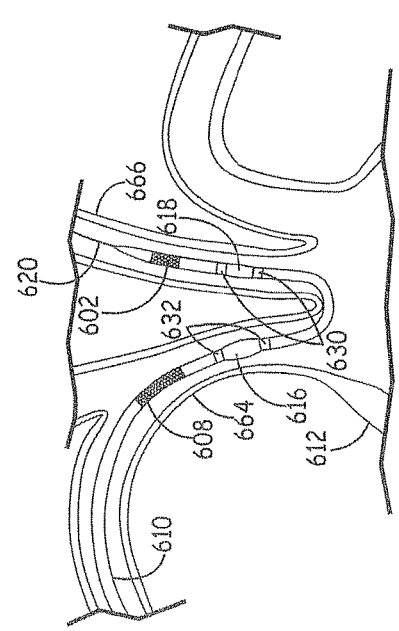

Referring to FIG. 7C, filtration catheter 610 is advanced along the guidewire 620 to position the distal filter element 602 and the distal balloon 618 into the left carotid artery 666, having the inflow opening 612 placed along the aortic arch, and the proximal balloon 616 and at least part of the proximal filter element 608 placed inside the brachiocephalic artery 664. Filtration catheter 610 is positioned to place the distal balloon 616 inside the left carotid artery 666 while having the proximal balloon 616 placed inside the brachiocephalic artery 664 to help properly position the inflow opening 612 inside the aortic arch, while having at least a portion of the proximal filter element 608 placed inside the brachiocephalic artery and the distal filter element 602 placed inside the left carotid. To help visualize the placement of the catheter during the delivery process, the distal balloon 618 is flanked by two radiopaque marker bands 630 while the proximal balloon 616 is flanked by two radiopaque marker bands 632, so the positions of the balloons will be visible with x-rays during the operation. The proximal balloon 616 is shown to be visibly longer (larger) than the distal balloon 618 while the proximal filter element 608 is shown to be visibly longer than the distal filter element 602.

Figure 7D:
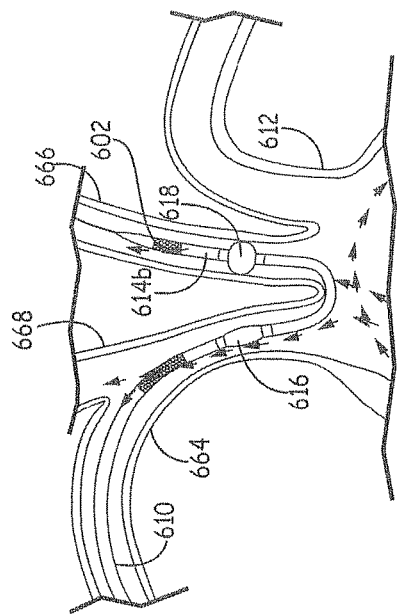

Referring to FIG. 7D, the distal balloon 618 is inflated to block direct blood flow into the left carotid artery 666. As shown by the arrows, while the natural blood flow is maintained in the aortic arch and brachiocephalic artery, some blood flow enters the inflow opening 612, flows through a distal conduit 614b and exits the distal filter element 602. In contrast, because the proximal balloon 616 is not yet inflated, the natural blood flow into brachiocephalic artery 664 is not blocked and re-directed and still flows freely without being filtered, by passing the filtration catheter 610 into the right carotid artery 668.

Figure 7E:
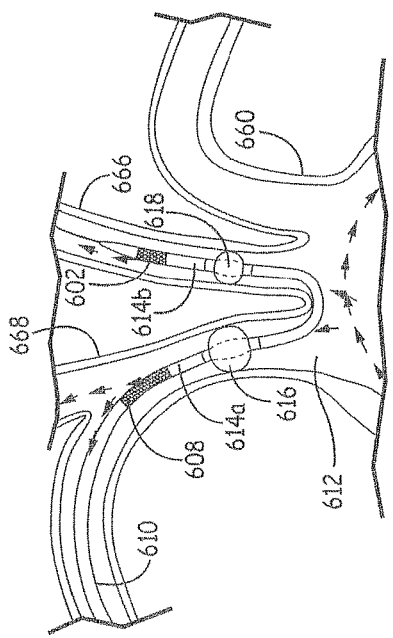

Referring to FIG. 7E, in addition to the distal balloon 618, the proximal balloon 616 is also inflated to block direct blood flow into the right carotid artery 668. As shown by the arrows, while the natural blood flow is maintained in the aortic arch 660, some blood flow enters the inflow opening 612, flows through a proximal conduit 614a and the distal conduit 614b and exits the proximal filter element 608 and the distal filter element 602 into the right carotid and the left carotid arteries 668 and 666 respectively. Because both the distal balloon and the proximal balloon elements are inflated and contact with the vessel walls, the filtration catheter 610 is relatively stationary inside the aortic arch 660, providing continuous filtration of the blood flowing from the aorta to the carotid arteries.

Figure 7F:
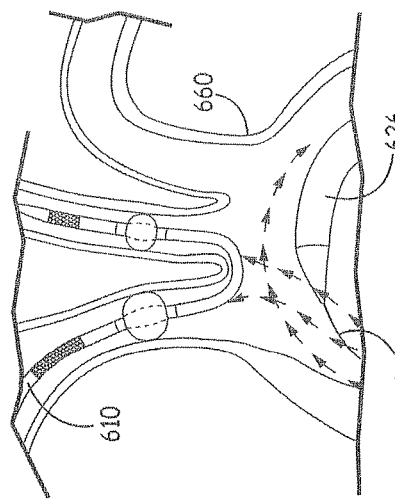
Figure 7G:
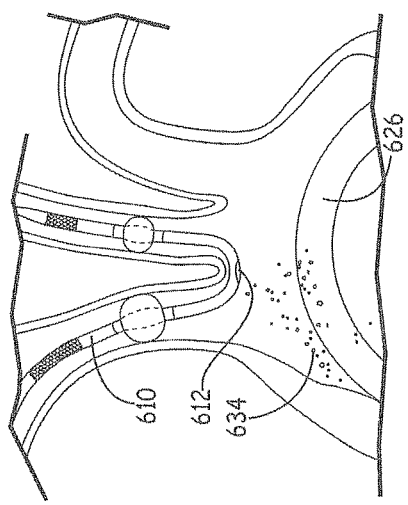
Figure 7H:
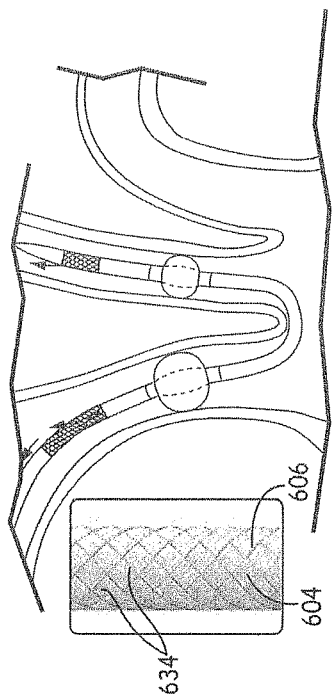
Figure 7I:
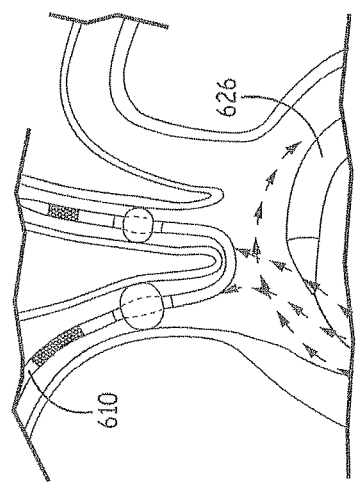

Referring to FIG. 7F, a treatment catheter 626 is delivered over the guide structure 624 to the aortic arch 660. As shown in FIG. 7F, there is no interference between the treatment catheter 626 and the filtration catheter 610. Referring to FIG. 7G, emboli 634 are generated by the treatment catheter 626 and enter the inflow opening 612 of the filtration catheter 610 along with the blood flow. Filtered blood exits the filter elements while the emboli are trapped inside the filter elements. FIG. 7H shows an enlarged section of filter element with interwoven polymer fibers 604 and diamond patterned metal filaments 606. Emboli 634 are shown to be captured by the filter element in the enlarged view.

Figure 7J:
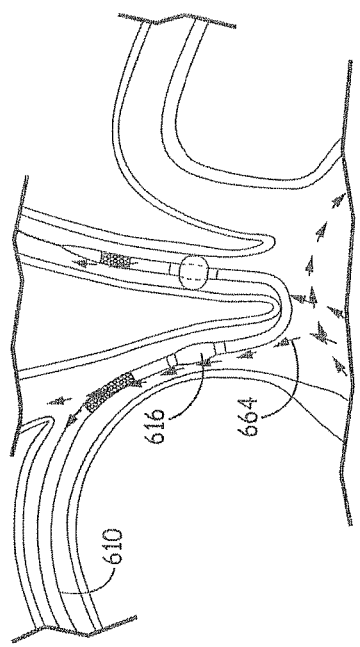
Figure 7K:
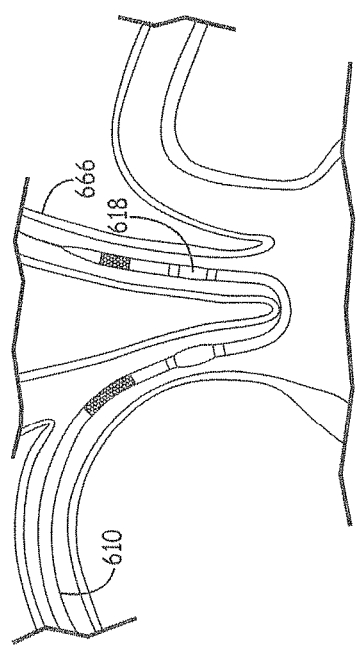
Figure 7L:
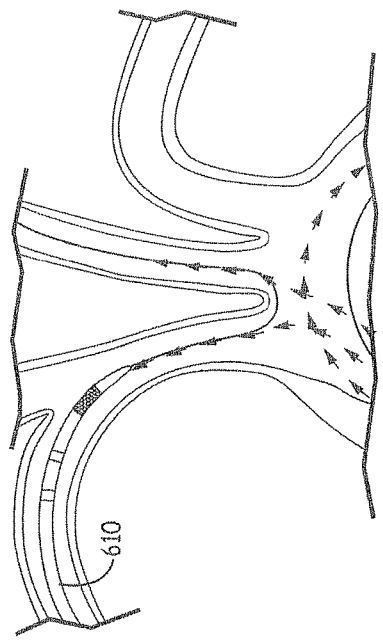

FIGS. 7I-7L illustrates retrieval process of the filtration catheter 610. Specifically, referring FIG. 7I, the treatment catheter 626 is retrieved from the aorta while the filtration catheter 610 is still deployed performing the filtration protection of carotid arteries. Once the treatment catheter is completely removed, the proximal balloon 616 is deflated as shown in FIG. 7J followed by the deflation of distal balloon 618 as shown in FIG. 7K, restoring natural blood flow into brachiocephalic artery 664 and left carotid artery 666 sequentially. Once both balloons are deflated, the filtration structure 610 is retrieved from the aorta as shown in FIG. 7L.

FIG. 8A is a schematic diagram illustrating the second type of filtration system 300 of FIGS. 4A-4G placed inside the aortic arch 360 by way of the right subclavian artery 362, with the proximal portion 336 of the filtration system placed outside the patient with shaft 306 extending into the patient. In some embodiment, once the filtration catheter 304 is successfully delivered and properly placed inside the brachiocephalic artery 364, the compliant balloon 316 can be inflated to anchor the filtration catheter 304 inside the brachiocephalic artery 364. Filter device 350 can be delivered through the main lumen 330 of the anchored filtration catheter 304 to enter the left carotid artery 366 through the aortic arch 360. As shown in FIG. 8A, when properly placed, distal opening 312 at the distal tip 322 of the filtration catheter 304 is located close to the entrance of the brachiocephalic artery 364, with the guide structure 320 of the filter device spanning between the entrances of the left carotid artery 366 and the brachiocephalic artery 364. The integrated filter element 308 and the balloon 316 are placed inside the brachiocephalic artery 364 with the integrated filter element 308 positioned proximally beyond the balloon 316. The independent filter element 352 with the distal tip 358 and strut 356 is placed inside the left carotid artery 366 with the filtration structure 354 of the independent filter element 352 deployed to contact the wall of the left carotid artery 366 to trap emboli. The filtration catheter and the filter device shown in FIG. 8A represent one embodiment of the second type of filtration system during an emboli protection procedure.

During the operation, on the right carotid artery 370 side, blood flow 368 in the aorta 360 is redirected by the distal balloon 316 to enter the distal opening 312 of the filtration catheter 304, travels through the conduit 314, and exit as filtered blood 372 through the integrated filter element 308 to enter into the right carotid artery 370. On the left carotid artery 366 side, blood flow 368 in the aorta 360 travels through the basket 354 of the independent filter element 352, and exits as filtered blood 374 to enter into the left carotid artery 366. The direction of the flow of the blood is indicated by black arrows in FIG. 8A.

Figure 8B:
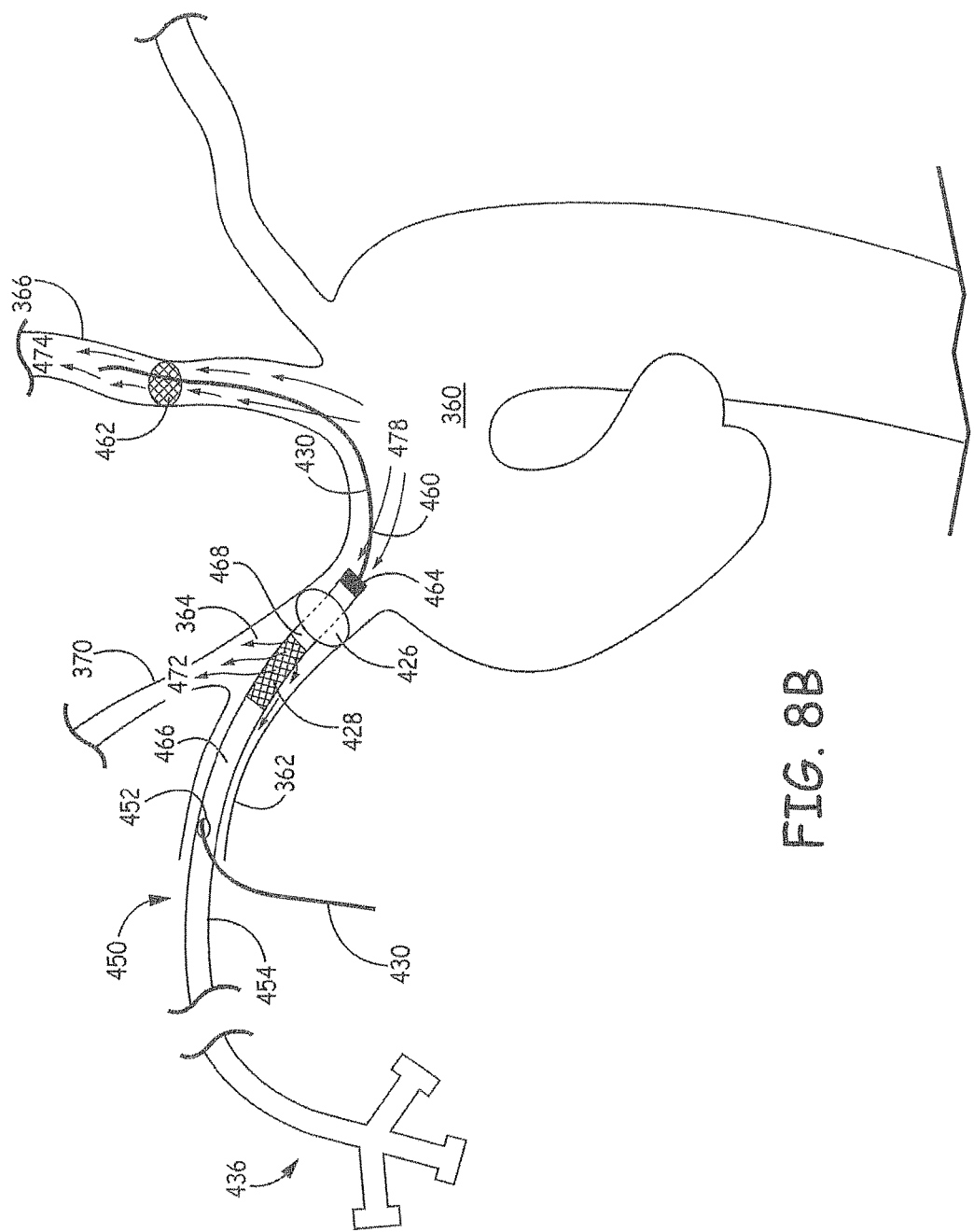
FIG. 8B is a schematic diagram illustrating a rapid exchange version of a second type of filtration system placed inside an aortic arch by way of the right subclavian artery.

FIG. 8B shows an alternative rapid exchange embodiment of filtration system 450 placed inside aortic arch 360 by way of the right subclavian artery 362, with a proximal portion 436 positioned outside the patient. Filtration catheter 454 comprises a rapid exchange guide wire port 452 that guide structure 430 of filter device 460 extends through. Proximal portion 436 may or may not comprise a main lumen if it is desirable to have access to the flow, such as for the delivery of a drug, contrast dye or aspiration. During delivery, the filtration catheter 454 can be pre-loaded with a filter device 460 and then the entire filtration system 450 can be delivered together, with the relative positions of the elements adjust as appropriate during delivery. The rest of the procedure should be very similar to the embodiment described in FIG. 8A, with the only difference being the rapid exchange configuration of the guide structure 430 relative to filtration catheter 454.

As shown in FIG. 8B, when properly placed, distal opening 464 of filtration catheter 454 is located close to the entrance of the brachiocephalic artery 364, with guide structure 430 of filter device 460 spanning between the entrances of the left carotid artery 366 and the brachiocephalic artery 364. Integrated filter element 428 and balloon 426 are positioned inside the brachiocephalic artery 364 with integrated filter element 462 positioned proximally relative to balloon 426. Alternatively, filter device 460 with guide structure 430 can be delivered and positioned inside aortic arch 360 and into left carotid artery 366 through brachiocephalic artery 364. With independent filter element 462 of filter device 460 successfully delivered and properly placed inside left carotid artery 366, filtration catheter 454 can then be delivered over guide structure 430 that extends through rapid exchange port 452. In general, the rapid exchange catheter embodiments can be designed with the guidewire extending through a main catheter lumen 466 or a distinct guidewire lumen. While shown in FIG. 8B with rapid exchange port 452 positioned in a proximal position relative to proximal filter 428, rapid exchange port 452 can be positioned at any point proximal to proximal occlusive element 426. Arrows 478 is used to indicate blood flow in the aorta that enters the inflow opening 464 of the filtration catheter 454, travels through the conduit 468 and exits as filtered blood flow 472 through integrated filter element 428 to enter into right carotid artery 370. On the left carotid side, arrows 478 are used to indicate blood flow in the aorta that enters left carotid artery 366 and filtered by independent filter element 462 and exit as filtered blood flow 474 into left carotid artery 366.

Figure 8C:
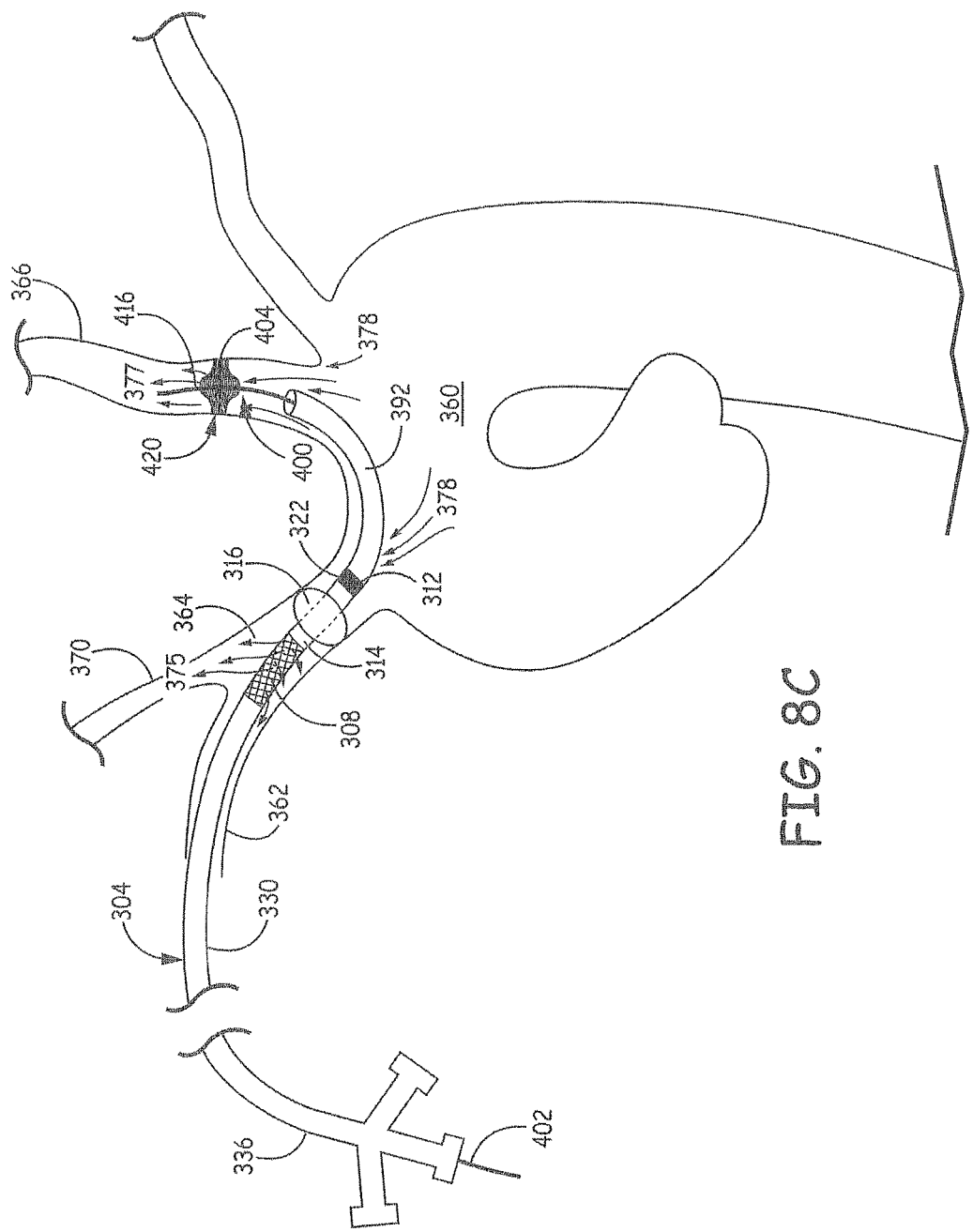
FIG. 8C is a schematic diagram illustrating an embodiment of a second type of filtration system comprising the filtration catheter of FIG. 4A and the filter device of FIG. 5G placed inside an aortic arch by way of the right subclavian artery with an retrieval catheter.

FIG. 8C is a schematic diagram illustrating another embodiment of the second type of filtration system with filtration catheter 304 used in conjunction with a filter device 400 in the vessels of a patient. The filtration catheter 304 can be delivered through right subclavian artery 362 and positioned similarly as described above while the proximal portion 336 remains outside the patient. The compliant balloon 316 can then be inflated to anchor the filtration catheter 304 inside the brachiocephalic artery 364. Filter device 400 can then be delivered through main lumen 330 of the anchored filtration catheter 304 to enter left carotid artery 366 through the aortic arch 360. As shown in FIG. 8C, when properly placed, the guide structure 402 of filter device 400 spans between the entrances of the left carotid artery 366 and the brachiocephalic artery 364. The independent filter element 420 with the distal tip 416 is placed inside the left carotid artery 366 with the fibers 404 of the independent filter element 420 deployed to contact the wall of the left carotid artery 366 to provide a porous three dimensional filtration matrix that comprises a plurality of pores that are sized to trap emboli. The filtration catheter and the filter device shown in FIG. 8C represent another embodiment of the second type of filtration system during an emboli protection procedure. Arrows 378 is used to indicate blood flow in the aorta that enters the inflow opening 312 at the distal tip 322 of the filtration catheter 304, travels through the conduit 314 and exits as filtered blood flow 375 through the integrated filter element 308 to enter into the right carotid artery 370. On the left carotid side, arrows 378 is used to indicate blood flow in the aorta that enters left carotid artery 366 and filtered by the independent filter element 420 and exit as filtered blood flow 377 into the left carotid artery 366. As shown in FIGS. 8A-C, the deployed filtration system occupies a small portion of the space inside the aortic arch with a portion of the guide structure, leaving the rest of the space for procedures, such as heart valve replacement or other procedures, e.g., endovascular procedures, on or in the vicinity of the heart. Because the filter element is an integral part of the filtration catheter, no deployment or collapse of the filter element associated with regular filters is involved. After the completion of the operation, the filter device can be retracted inside the filtration catheter and the entire system can be simply removed with the emboli trapped inside the independent filter element as well as the conduit or within the braids or waves of the fibers, although in other embodiments, a separate retrieval catheter, aspiration catheter or the like can be used in addition to or as an alternative to the use of the filtration catheter to facilitate removal of the independent filter. During recovery, a catheter and/or sheath can be used to retrieve the independent filter element of a filtration system as an alternative or in addition to the filtration catheter or other retrieval tools. For example, as shown in FIG. 8C, a catheter 392 can be delivered through the lumen of the filtration catheter 304 along the guide structure 402 of the independent filter element 420 to collapse the fiber bundles 404 into a retrieval configuration or generally cover the filter element if already in a retrieval configuration through the manipulation of the guide structure 402 alone. Suction can additionally be applied through the catheter 392 to prevent the release of emboli during the retrieval process. The use of suction for the recovery of a filter device has been discussed for example in U.S. Pat. No. 8,021,351 to Boldenow et al., entitled "Tracking Aspiration Catheter," and published U.S. patent application 2005/0277976 to Galdonik et al., entitled "Emboli Filter Export System," both of which are incorporated herein by reference.

Figure 9A:
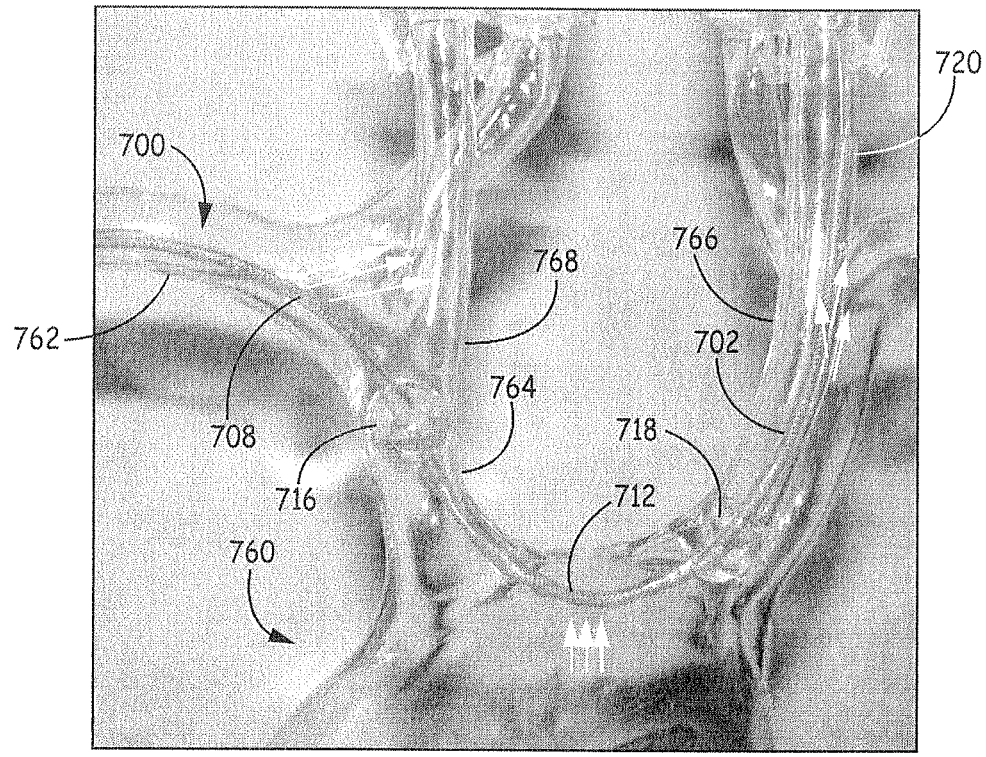
FIG. 9A is a photograph of an embodiment of the first type of filtration catheter placed inside a glass scale model of aortic arch by way of the model right subclavian artery.
Figure 9B:
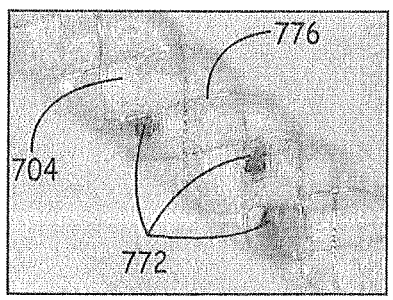
FIG. 9B is a photograph of a section of filter element of the filtration catheter of FIG. 9A with emboli trapped inside the interwoven fibers of the filter elements of the filtration catheter.

Examples of devices of the first and the second type filter systems are constructed based on the disclosure herein. The examples of devices were then placed inside glass model of aortic arch to simulate blood filtration/emboli capturing process in an actual aorta. FIG. 9A is a photo of a first type of filtration catheter 700 placed inside a glass model of aortic arch 760 by way of the model right subclavian artery 762, showing the inflated proximal balloon 716 inside the brachiocephalic artery 764 and the inflated distal balloon 718 inside the left carotid artery 766 and guidewire 720 extending from the distal portion of the catheter. Fluid mimicking blood with emboli is pumped to circulate the glass model mimicking the blood flow condition in an actual aorta. As indicated by blank arrows in FIG. 9A, blood with emboli enters into the inflow opening 712, is filtered by the filter elements 708 and 702 and enters into the carotid arteries 768 and 766 respectively. FIG. 9B shows a photo of a section of filter element with emboli 772 trapped inside the interwoven fibers 704. The enlarged section of filter element also reveals diamond patterned metal wires or filaments 776 integrated into the interwoven fibers 704 of the filter element to provide structural integrity for the filter element.

Figure 10A:
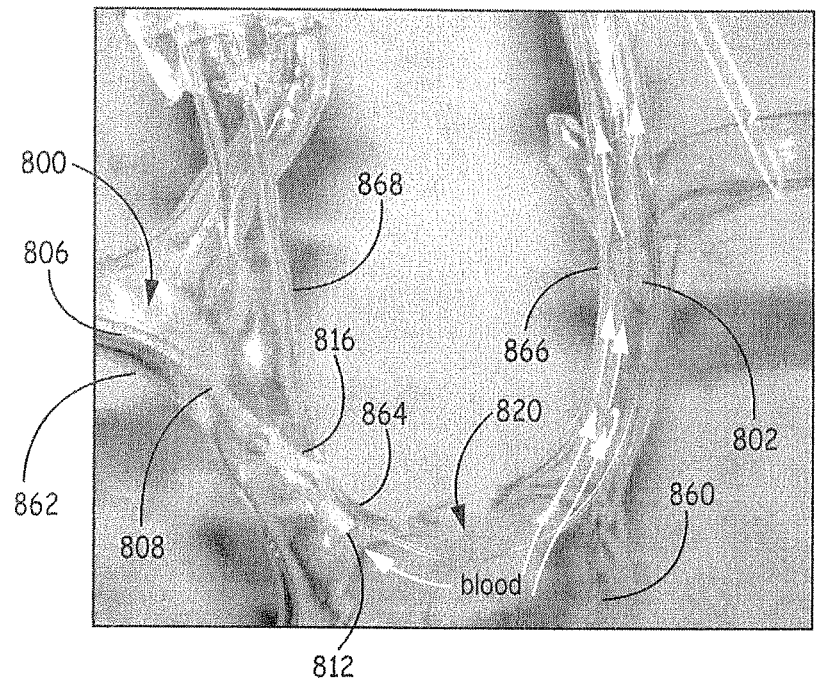
FIG. 10A is a photograph of an embodiment of the second type of the filtration system placed inside a glass scale model of aortic arch by way of the model right subclavian artery.
Figure 10B:
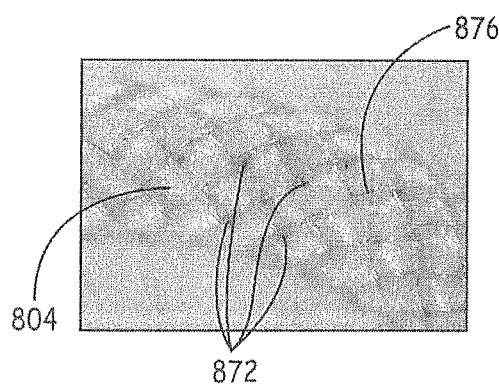
FIG. 10B is a photograph of a section of filter element of the filtration catheter of FIG. 10A with emboli trapped inside the interwoven fibers of the integrated filter element of the filtration catheter.

FIG. 10A is a photo of an embodiment of a second type of filtration system 800 placed inside a glass model of aortic arch 860 by way of the model right subclavian artery 862, showing the filtration catheter 806 is anchored by the inflated balloon 816 inside the brachiocephalic artery 864 and the deployed independent filter element 802 inside the left carotid artery 866 and guide structure 820 spanning the aortic arch 860. The independent filter element 802 attached to the guide structure 820 is delivered through the filtration catheter 806. The filter element 802 is shown to have a basket type of structure formed with metal mesh with the opening of the basket facing the aorta. Fluid mimicking blood with emboli indicated by arrows is pumped to circulate the glass model mimicking the blood flow condition in an actual aorta. As indicated by arrows in FIG. 10A, on the brachiocephalic artery 864 side, blood with emboli enters into the distal inflow opening 812 of the filtration catheter 806, is filtered by the filter element 808 and enters into the right carotid artery 868. On the left carotid artery 866 side, blood with emboli is filtered by basket mesh of the independent filter element 802, and enters into the left carotid artery 866. FIG. 10B shows photos of a section of the integrated filter element 808 with emboli 872 trapped inside the interwoven fibers 804. The enlarged interwoven fibers also reveal diamond patterned metal wires or filaments 876 integrated into the interwoven fibers 804 of the filter element to provide structural integrity for the filter element.

Performance

The devices described herein can be configured to trap a substantial majority of emboli or particulates while maintain blood flow through the filter elements into the carotid arteries. The materials and structure of the device can be selected to have porosity that would allow passage of blood components, such as white blood cells (about 7-20 microns), red blood cells (8-9 microns) and platelets (2-4 microns), yet collects emboli. The filters described herein are generally designed to trap a substantial majority of emboli with an average diameter of at least 100 microns. A substantial majority of particulates can be considered to be at least about 95 percent and in further embodiments at least about 99.5 percent of all the particulates flowed through. In some embodiment, the speed and volume of blood flow through the filter elements are substantially unchanged compared to without filtration. In some embodiments, the blood flow through the filter elements maintains at least 50% of the original unfiltered blood flow in volume per unit time, in other embodiments, at least 75%, in additional embodiments at least 85% relative to the natural flow through the respective vessel. A person of ordinary skill in the art will recognize that additional ranges of particulate trapping and percentage of flow maintained within the explicit ranges above are contemplated and are within the present disclosure.

Sterilization and Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together. Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package. In general, the filtration systems disclosed herein are for single use.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A filtration system comprising:
    a biocompatible filtration catheter comprising:
        a shaft having a balloon lumen, a proximal end and a distal end;
        a proximal port in fluid communication with the balloon lumen and connected to the proximal end of the shaft;
        an integrated filter element having an inner flow lumen integrated as part of a wall of the catheter at or near the distal end of the shaft, wherein the integrated filter element provides for fluid flow out from the catheter interior;
        a distal section extending in a distal orientation from the integrated filter element and having a distal opening, wherein a tubular portion of the balloon lumen extends along the integrated filter element through the inner flow lumen from the shaft to the distal section;
        a balloon having an interior in fluid communication with the balloon lumen and that is associated with an exterior of the distal section at or near the distal end of the distal section that can extend radially outward from the exterior of and around the circumference of the shaft; and
        a conduit extending within the distal section from the distal opening to the inner flow lumen of the integrated filter element to provide fluid communication between the distal opening and the integrated filter element; and
    a filter device comprising a guide structure and an independent filter element supported by the guide structure, wherein the filtration catheter comprises a central lumen that is suitable for the delivery of the independent filter element mounted on the guide structure through the distal opening of the shaft.

2. The filtration system of claim 1 wherein the independent filter element comprises surface capillary fibers having a first configuration in a bundle with a low profile configuration and an extended configuration with the fibers flaring outward from the guide structure, wherein the guide structure comprises a corewire and an overtube with the corewire extending through a lumen of the overtube, and wherein the relative movement of the corewire and the overtube transitions the fibers from the low profile configuration to the extended configuration.

3. The filtration system of claim 1 wherein the independent filter element comprises a filter basket.

4. The filtration system of claim 3 wherein the filter basket comprises an opening into the filter basket oriented toward the proximal end of the guide structure.

5. The filtration system of claim 4 wherein the filter basket comprises a strut configures to collapse the filter to a recovery configuration with the advancement of a retrieval catheter.

6. The filtration system of claim 4 wherein the filter basket comprises a distal tip extending beyond the distal end of the filter basket.

7. The filtration system of claim 1 further comprising an aspiration catheter with dimension providing for placement over the guide structure and delivery through the lumen of the filtration catheter.

8. The filtration system of claim 1 wherein the integrated filter element comprises interwoven fibers.

9. The filtration system of claim 8 wherein the interwoven fibers further comprises metal filaments.

10. The filtration system of claim 8 wherein the interwoven fibers further comprises surface capillary fibers.

11. The filtration system of claim 8 wherein the interwoven fibers have a diameter from 5 microns to about 150 microns.

12. The filtration system of claim 1 wherein the integrated filter element having a length from about 10 mm to about 70 mm.

13. The filtration system of claim 1 wherein the integrated filter element has pore sizes of about 50 micron to about 500 micron.

14. The filtration system of claim 1 wherein the shaft comprises an outer diameter and wherein the integrated filter element comprises an outer diameter approximately the same as the outer diameter of the shaft and wherein the integrated filter element has structural stability.

15. The filtration system of claim 1 wherein the balloon has an extended configuration with a diameter suitable to occlude a human brachiocephalic artery.

16. The filtration system of claim 1 wherein the balloon comprises a compliant deformable material connected to the shaft to provide for inflation of the balloon.

17. The filtration system of claim 1 wherein the catheter has a diameter between about 5 Fr to about 7 Fr.

18. The filtration system of claim 1 further comprising a sheath slidably positioned over the catheter having a configuration extended in a distal direction relative to the catheter covering the integrated filter element.

* * * * *